United States Patent
Bodurka et al.

(10) Patent No.: US 12,190,712 B2
(45) Date of Patent: *Jan. 7, 2025

(54) PATIENT SUPPORT APPARATUSES WITH NURSE CALL CONNECTION DETECTION

(71) Applicant: Stryker Corporation, Kalamzoo, MI (US)

(72) Inventors: Alexander Josef Bodurka, Portage, MI (US); Jerald A. Trepanier, Kalamazoo, MI (US); Krishna Sandeep Bhimavarapu, Kalamazoo, MI (US); Scott Kuebler, Delton, MI (US)

(73) Assignee: Stryker Corporation, Portage, MI (US)

( * ) Notice: Subject to any disclaimer, the term of this patent is extended or adjusted under 35 U.S.C. 154(b) by 322 days.

This patent is subject to a terminal disclaimer.

(21) Appl. No.: 17/640,120

(22) PCT Filed: Sep. 3, 2020

(86) PCT No.: PCT/US2020/049125
§ 371 (c)(1),
(2) Date: Mar. 3, 2022

(87) PCT Pub. No.: WO2021/046171
PCT Pub. Date: Mar. 11, 2021

(65) Prior Publication Data
US 2022/0301416 A1 Sep. 22, 2022

Related U.S. Application Data

(60) Provisional application No. 62/896,075, filed on Sep. 5, 2019.

(51) Int. Cl.
*G08B 21/00* (2006.01)
*G08B 26/00* (2006.01)
*G16H 40/63* (2018.01)

(52) U.S. Cl.
CPC ............ *G08B 26/008* (2013.01); *G16H 40/63* (2018.01)

(58) Field of Classification Search
CPC ...... G08B 26/008; G16H 40/63; G16H 40/67; A61G 2203/30; A61G 2203/70; A61G 2205/60; A61G 7/05
(Continued)

(56) References Cited

U.S. PATENT DOCUMENTS 6,067,014 A   5/2000 Wilson
7,352,289 B1  4/2008 Harris
(Continued)

FOREIGN PATENT DOCUMENTS

WO    1994027544    12/1994

OTHER PUBLICATIONS

PCT International Search Report dated Oct. 26, 2020, for International application No. PCT/US20/49125.
(Continued)

*Primary Examiner* — Mark S Rushing
(74) *Attorney, Agent, or Firm* — Warner Norcross + Judd LLP

(57) ABSTRACT

A patient support apparatus includes a frame, a patient support surface, and a nurse call cable interface adapted to communicatively couple to a wall-mounted nurse call outlet having a plurality of pins to thereby allow the patient to communicate with a remotely positioned nurse. One or more sensors are included that detect when the cable is plugged into the nurse call outlet and/or when the bed is communicatively coupled to the nurse call system. The controller may activate an indicator when the sensor detects that the bed is not coupled to the nurse call system outlet, automatically select whether to communicate with the nurse call system via a wireless transceiver or via the nurse call cable interface
(Continued)

based on the sensor output, and/or inform the caregiver when a headwall module spaced from the bed is not communicatively coupled to the nurse call system outlet.

18 Claims, 12 Drawing Sheets

(58) Field of Classification Search
USPC .................................................... 340/286.07
See application file for complete search history.

(56) References Cited

U.S. PATENT DOCUMENTS

| | | |
|---|---|---|
| 9,999,375 B2 | 6/2018 | Hayes et al. |
| 10,235,845 B2 | 3/2019 | Bhimavarapu et al. |
| 10,257,063 B2 | 4/2019 | Bhimavarapu et al. |
| 2007/0141869 A1 | 6/2007 | McNeely et al. |
| 2009/0063183 A1 | 3/2009 | McNeely et al. |
| 2014/0259410 A1 | 9/2014 | Zerhusen et al. |
| 2016/0038361 A1* | 2/2016 | Bhimavarapu .......... H04B 7/24 |
| 2017/0221344 A1* | 8/2017 | Cox ....................... G08B 25/10 |
| 2019/0046379 A1 | 2/2019 | Constant et al. |
| 2019/0150737 A1 | 5/2019 | Bodurka et al. |
| 2019/0183705 A1 | 6/2019 | Bodurka |
| 2019/0188992 A1 | 6/2019 | Bodurka et al. |

OTHER PUBLICATIONS

PCT International Written Opinion dated Oct. 26, 2020, for International application No. PCT/US20/49125.

* cited by examiner

Side View

End View

Pin 1  Bed Monitoring Status On
Pin 2  Read Light
Pin 3  Room Light
Pin 4  Speaker High
Pin 5  Potentiometer Wiper
Pin 6  Bed Exit Status On
Pin 7  Nurse Call Interlock
Pin 8  Audio Transfer -
Pin 9  Audio Transfer +
Pin 10 Interlock +
Pin 11 Interlock -
Pin 12 Bed Monitoring Fowler 30 deg. Alert
Pin 13 No Connect
Pin 14 Potentiometer Low Common
Pin 15 Potentiometer High Common (Std.) / Audio (STV)
Pin 16 Nurse Answer Light +
Pin 17 Bed Monitor Alert
Pin 18 Bed Monitoring Siderail Alert
Pin 19 Nurse Call Light +
Pin 20 No Connect
Pin 21 No Connect
Pin 22 No Connect
Pin 23 Brake Status On
Pin 24 No Connect
Pin 25 Nurse Call +
Pin 26 Nurse Call NO/NC
Pin 27 Room/Read Light Common
Pin 28 Nurse Call Light -
Pin 29 Nurse Answer Light -
Pin 30 Priority NO/NC
Pin 31 Priority Common
Pin 32 Bed Monitoring Low Height Alert
Pin 33 TV - (Std.) / Data (STV)
Pin 34 TV + (Std.) / Common (STV)
Pin 35 Speaker Low Common
Pin 36 Audio Shield
Pin 37 Bed Monitoring Common FIG. 17
(Prior Art)

PATIENT SUPPORT APPARATUSES WITH NURSE CALL CONNECTION DETECTION

CROSS-REFERENCE TO RELATED APPLICATIONS

This application claims priority to U.S. provisional patent application Ser. No. 62/896,075 filed Sep. 5, 2019, by inventors Alexander Bodurka et al. and entitled PATIENT SUPPORT APPARATUSES WITH NURSE CALL CONNECTION DETECTION, the complete disclosure of which is incorporated herein by reference.

BACKGROUND

The present disclosure relates to patient support apparatuses, such as beds, cots, stretchers, recliners, or the like. More specifically, the present disclosure relates to patient support apparatuses that are adapted to communicate with an existing nurse call system.

Existing hospital beds often include an exit detection system that detects when the patient leaves the bed and notifies a nurse call system that the patient has left the bed. Existing hospital beds also often include a nurse call button and a speaker that together allow the patient to communicate with a remote nurse using the nurse call system. Still other features and/or information regarding the bed may also be communicated to and/or through the nurse call system, or to a room interface board that controls various aspects of the room in which the patient support apparatus is positioned (e.g. volume, channel, and power of a television, room temperature, room lights, etc.).

In many existing hospitals, the conventional nurse call system includes a cord-out sensor that detects when a nurse call cable between the bed and a nurse call outlet gets disconnected from the nurse call outlet. Often, an alert is issued by the nurse call system when the cord-out sensor detects that the nurse call cable is disconnected from the nurse call outlet. However, many nurse call systems include a cancel or override feature that shuts down this cord-out alert when the caregiver desires to remove the cable from the nurse call outlet. It is therefore possible for beds to be positioned within a room without having their nurse call cable plugged into the nurse call outlet, and without having any alert issued by the nurse call system to appropriate caregivers.

SUMMARY

According to various embodiments, the present disclosure provides one or more improved features for detecting when a patient support apparatus is connected to, and/or disconnected from, a conventional nurse call system. In at least one embodiment, the present disclosure provides a patient support apparatus that includes one or more cable sensors to detect when a nurse call cable is coupled to the patient support apparatus. Alternatively, or additionally, the patient support apparatus may include a communication sensor that detects when a communication channel has been established between the patient support apparatus and the nurse call system. Still further, the patient support apparatus may be configured to automatically select using wired or wireless communication to communicate with the nurse call system based upon the detection of a cable and/or a wired communication channel, or the lack of detection of a cable and/or a wired communication channel. Still other features and functions may be provided, as will be apparent from the following description.

According to one embodiment of the present disclosure, a patient support apparatus is provided that includes a litter frame, a support deck, a nurse call cable interface, a cable sensor, an indicator, and a controller. The support deck is supported by the litter frame and adapted to support a patient thereon. The nurse call cable interface is adapted to receive a first end of a nurse call cable. The nurse call cable includes a second end adapted to couple to an outlet of a nurse call system. The outlet may be mounted to a headwall of a healthcare facility. The cable sensor is adapted to detect when the nurse call cable is physically coupled to the nurse call cable interface and when the nurse call cable is not physically coupled to the nurse call cable interface. The controller is adapted to activate the indicator when the cable sensor detects that the nurse call cable is not physically coupled to the nurse call cable interface.

According to other aspects of the present disclosure, the cable sensor may include one or more of the following: a Hall effect sensor adapted to detect a presence of the first end of the nurse call cable when the first end of the nurse call cable is plugged into the nurse call cable interface; an inductive sensor adapted to detect a presence of the first end of the nurse call cable when the first end of the nurse call cable is plugged into the nurse call cable interface; a Reed switch sensor adapted to detect a presence of the first end of the nurse call cable when the first end of the nurse call cable is plugged into the nurse call cable interface; and/or an optical sensor adapted to detect a presence of the first end of the nurse call cable when the first end of the nurse call cable is plugged into the nurse call cable interface.

In some embodiments, the first end of the nurse call cable includes a 37-pin connector, the nurse call cable interface includes a port adapted to couple to the 37-pin connector, and the patient support apparatus further comprises a communication sensor adapted to detect when a communication channel is successfully established between the nurse call cable interface and the nurse call system.

In some embodiments, the communication sensor is a voltage sensor adapted to detect voltage on two of the pins, and the controller is adapted to conclude that the communication channel is successfully established when voltage is detected on either or both of the two pins. A first one of the two pins may be a Nurse Call Plus pin and a second one of the two pins may be a Priority Normally Open/Normally Closed (NO/NC) pin.

In some embodiments, the patient support apparatus further includes a display in communication with the controller. The controller is adapted to display a dismissable popup window on the display when the cable sensor detects that the nurse call cable is not physically coupled to the nurse call cable interface.

The indicator may comprise a light adapted to illuminate a nurse call connection icon. In such embodiments, the controller may activate the light with a green color when the nurse call cable is physically coupled to the nurse call cable interface, and with a different color (or no color) when the nurse call cable is not physically coupled to the nurse call cable interface. The different color, in some embodiments, is amber.

In some embodiments, the patient support apparatus further includes a wireless network transceiver adapted to communicate with a server on a local area network via a wireless access point of the local area network. In such embodiments, the controller is further adapted to send a message to the server when the sensor detects that the nurse call cable is not physically coupled to the nurse call cable interface.

The patient support apparatus may further include a wireless transceiver adapted to wirelessly communicate with a headwall module mounted to the headwall of the healthcare facility. In such embodiments, the controller may be adapted to automatically send data to the nurse call system via the wireless transceiver when the sensor detects the nurse call cable is not physically coupled to the nurse call cable interface, and to automatically send data to the nurse call system via the nurse call cable interface when the sensor detects the nurse call cable is physically coupled to the nurse call cable interface.

In some embodiments, the wireless transceiver is a Bluetooth transceiver. Still further, in some embodiments, the patient support apparatus may further comprise an infrared transceiver adapted to communicate with the headwall module. In such embodiments, the controller automatically pairs the patient support apparatus with the headwall module using information received from the headwall module via the infrared transceiver.

A patient support apparatus according to another embodiment of the present disclosure includes a litter frame, a support deck, a nurse call cable interface, a communication sensor, an indicator, and a controller. The support deck is supported by the litter frame and is adapted to support a patient thereon. The nurse call cable interface is adapted to receive a first end of a nurse call cable. The nurse call cable includes a second end adapted to couple to an outlet of a nurse call system. The outlet may be mounted to a headwall of a healthcare facility. The communication sensor is adapted to detect when a communication channel is successfully established between the nurse call cable interface and the nurse call system, and to detect when the communication channel is not successfully established between the nurse call cable interface and the nurse call system. The controller is adapted to activate the indicator when the communication sensor detects that the communication channel is not successfully established between the nurse call cable interface and the nurse call system.

According to other aspects, the first end of the nurse call cable may include a 37-pin connector and the nurse call cable interface may include a port adapted to couple to the 37-pin connector. In such cases, the communication sensor may be a voltage sensor adapted to detect voltage on two of the pins. Further, the controller may be adapted to conclude that the communication channel is successfully established when voltage is detected on either or both of the two pins. In some embodiments, a first one of the two pins is a Nurse Call Plus pin and a second one of the two pins is a Priority Normally Open/Normally Closed (NO/NC) pin.

In some embodiments, the patient support apparatus further includes a display in communication with the controller. The controller is adapted to display a dismissable popup window on the display when the communication sensor detects that the communication channel is not successfully established between the nurse call cable interface and the nurse call system.

In some embodiments, the indicator comprises a light adapted to illuminate a nurse call connection icon.

In some embodiments, the patient support apparatus further includes a wireless network transceiver adapted to communicate with a server on a local area network via a wireless access point of the local area network. In such embodiments, the controller is further adapted to send a message to the server when the communication sensor detects that the communication channel is not successfully established between the nurse call cable interface and the nurse call system.

The patient support apparatus may further include a wireless transceiver adapted to wirelessly communicate with a headwall module mounted to the headwall of the healthcare facility. In such embodiments, the controller may be adapted to automatically send data to the nurse call system via the wireless transceiver when the communication sensor detects that the communication channel is not successfully established between the nurse call cable interface and the nurse call system, and to automatically send data to the nurse call system via the nurse call cable interface when the communication sensors detects that the communication channel is successfully established between the nurse call cable interface and the nurse call system.

In some embodiments, the patient support apparatus also includes a cable sensor adapted to detect when the nurse call cable is physically coupled to the nurse call cable interface and when the nurse call cable is not physically coupled to the nurse call cable interface. The cable sensor may be any one of more of (a) a Hall effect sensor adapted to detect a presence of the first end of the nurse call cable when the first end of the nurse call cable is plugged into the nurse call cable interface; (b) an inductive sensor adapted to detect a presence of the first end of the nurse call cable when the first end of the nurse call cable is plugged into the nurse call cable interface; (c) a Reed switch sensor adapted to detect a presence of the first end of the nurse call cable when the first end of the nurse call cable is plugged into the nurse call cable interface; and/or (d) an optical sensor adapted to detect a presence of the first end of the nurse call cable when the first end of the nurse call cable is plugged into the nurse call cable interface.

A patient support apparatus according to another embodiment of the present disclosure includes a litter frame, a support deck, an exit detection system, a nurse call cable interface, a wireless transceiver, and a controller. The support deck is supported by the litter frame and is adapted to support a patient thereon. The exit detection system is adapted to issue an alert when the exit detection system is armed and the patient exits the patient support apparatus. The nurse call cable interface is adapted to receive a first end of a nurse call cable. The nurse call cable includes a second end adapted to couple to an outlet of a nurse call system. The outlet may be mounted to a headwall of a healthcare facility. The wireless transceiver is adapted to wirelessly communicate with a headwall module mounted to the headwall of the healthcare facility. The headwall module is adapted to be physically coupled to the outlet. The controller is adapted to alert the nurse call system when the exit detection system detects the patient has exited the patient support apparatus. The controller is further adapted to automatically select whether to communicate the alert to the nurse call system via the wireless transceiver or via the nurse call cable interface.

According to other aspects of the present disclosure, the patient support apparatus further includes a cable sensor adapted to detect when the nurse call cable is physically coupled to the nurse call cable interface and when the nurse call cable is not physically coupled to the nurse call cable interface. In such embodiments, the controller automatically selects to communicate the alert to the nurse call system via the nurse call cable interface when the cable sensor detects that the nurse call cable is physically coupled to the nurse call cable interface. Additionally, or alternatively, the controller automatically selects to communicate the alert to the nurse call system via the wireless transceiver when the cable sensor detects that the nurse call cable is not physically coupled to the nurse call cable interface.

In some embodiments, the patient support apparatus further comprises a communication sensor adapted to detect when a communication channel is successfully established between the nurse call cable interface and the nurse call system, and to detect when the communication channel is not successfully established between the nurse call cable interface and the nurse call system. In such embodiments, the controller automatically selects to communicate the alert via the wireless transceiver when the communication sensor detects that the communication channel is not successfully established between the nurse call cable interface and the nurse call system. The controller may additionally, or alternatively, be configured to automatically select to communicate the alert via the nurse call cable interface when the communication sensor detects that the communication channel is successfully established between the nurse call cable interface and the nurse call system.

In some embodiments, the patient support apparatus includes a Bluetooth transceiver and an infrared transceiver that are both adapted to communicate with a headwall module. In such embodiments, the controller automatically pairs the patient support apparatus with the headwall module using information received from the headwall module via the infrared transceiver.

In some embodiments, the patient support apparatus includes a wireless transceiver that is adapted to receive a message from the headwall module, the message indicating at least one of the following: (a) the headwall module is not physically coupled to the outlet of the nurse call system, or (b) the headwall module is not physically coupled to the outlet of the nurse call system. The controller, in such embodiments, is adapted to use the message when selecting whether to communicate the alert to the nurse call system via the wireless transceiver or via the nurse call cable interface.

A patient support apparatus according to another embodiment of the present disclosure includes a litter frame, a support deck, a nurse call cable interface, a sensor, a wireless transceiver, a user interface, and a controller. The support deck is supported by the litter frame and is adapted to support a patient thereon. The nurse call cable interface is adapted to receive a first end of a nurse call cable. The nurse call cable includes a second end adapted to couple to an outlet of a nurse call system. The outlet may be mounted to a headwall of a healthcare facility. The sensor is adapted to detect if the nurse call cable interface is communicatively coupled to the outlet. The wireless transceiver is adapted to wirelessly communicate with a headwall module mounted to the headwall of the healthcare facility. The headwall module is adapted to be physically coupled to the outlet, and the wireless transceiver is adapted to receive a message from the headwall module indicating that the headwall module is not communicatively coupled to the outlet of the nurse call system. The controller is adapted to control the user interface to inform the caregiver when the sensor detects that the nurse call cable interface is not communicatively coupled to the outlet and to inform the caregiver when the wireless transceiver receives the message indicating that the headwall module is not communicatively coupled to the outlet of the nurse call system.

According to other aspects of the present disclosure, the patient support apparatus further comprises a first indicator and a second indicator. The controller is adapted to activate the first indicator when the sensor detects that the nurse call cable interface is not communicatively coupled to the outlet and to activate the second indicator when the wireless transceiver receives the message indicating that the headwall module is not communicatively coupled to the nurse call system.

In some embodiments, the user interface includes a display and the controller is adapted to display a first message on the display when the sensor detects that the nurse call cable interface is not communicatively coupled to the outlet and to display a second message on the display when the wireless transceiver receives the message indicating that the headwall module is not communicatively coupled to the nurse call system.

In some embodiments, the sensor is a communication sensor adapted to detect when a communication channel is successfully established between the nurse call cable interface and the nurse call system, and to detect when the communication channel is not successfully established between the nurse call cable interface and the nurse call system.

In some embodiments, the sensor is a cable sensor adapted to detect when the nurse call cable is physically coupled to the nurse call cable interface and when the nurse call cable is not physically coupled to the nurse call cable interface.

In any of the embodiments disclosed herein, the principles of the present disclosure may be alternatively applied to a stretcher, a chair, a cot, and/or a recliner, or another type of patient support apparatus that is adapted to communicate with a nurse call system outlet.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 17 is a chart of a prior art example of the functions of the pins of a 37-pin cable often used in existing healthcare facilities.

DETAILED DESCRIPTION OF THE EMBODIMENTS

Figure 1:
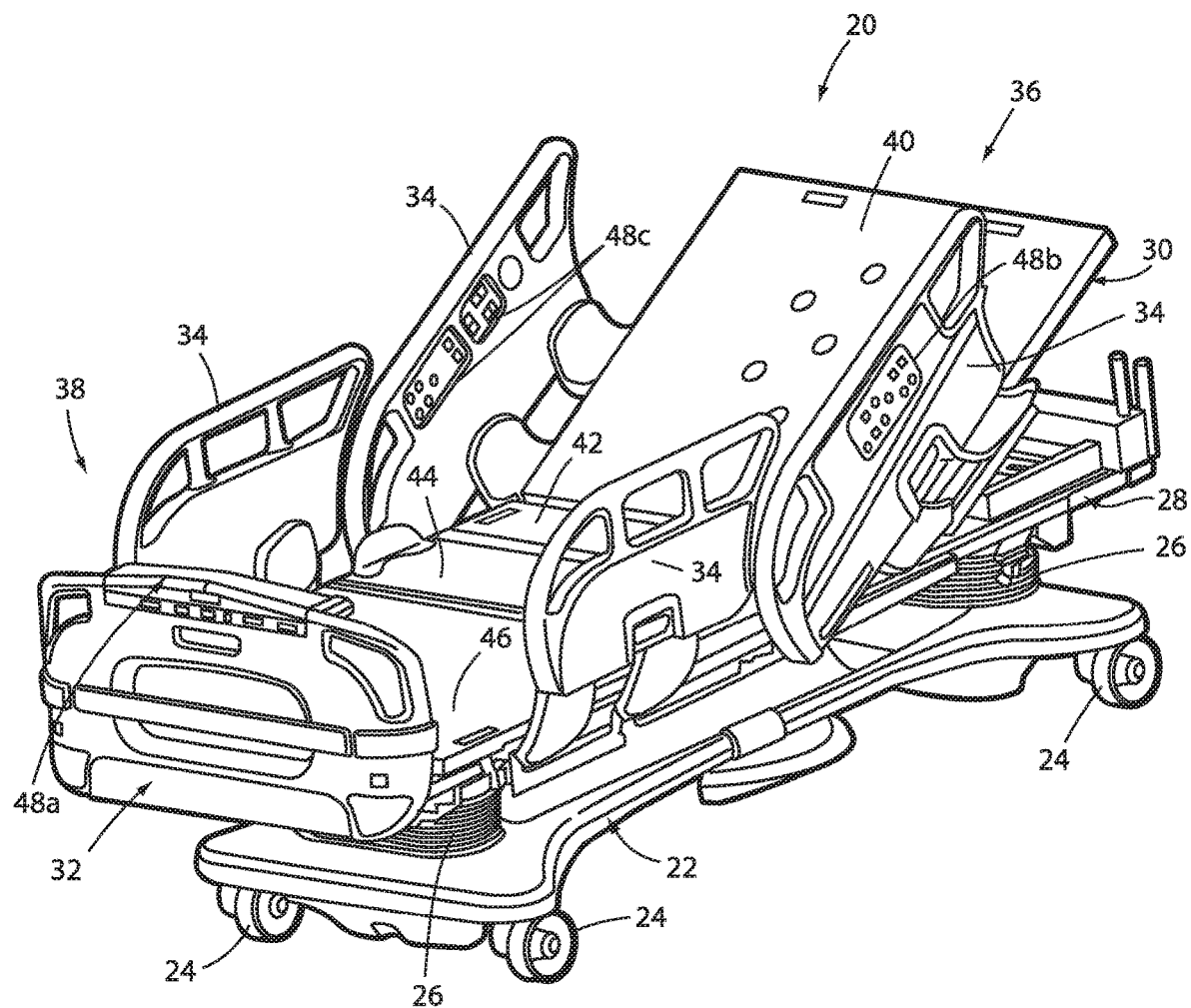
FIG. 1 is a perspective view of a patient support apparatus according to a first embodiment of the present disclosure.

An illustrative patient support apparatus 20 according to a first embodiment of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a recliner, a chair, or any other patient support structure that communicates with a nurse call outlet of a conventional nurse call system.

In general, patient support apparatus 20 includes a base 22 having a plurality of wheels 24, a pair of lifts 26 supported on the base 22, a litter frame 28 supported on the lifts 26, and a support deck 30 supported on the litter frame 28. Patient support apparatus 20 further includes a footboard 32 and a plurality of side rails 34. Side rails 34 are all shown in a raised position in FIG. 1 but are each individually movable to a lower position in which ingress into, and egress out of, patient support apparatus 20 is not obstructed by the lowered side rails 34.

Lifts 26 are adapted to raise and lower litter frame 28 with respect to base 22. Lifts 26 may be hydraulic actuators, pneumatic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end 36 and a foot end 38, each of whose height can be independently adjusted by the nearest lift 26. Patient support apparatus 20 is designed so that when an occupant lies thereon, his or her head will be positioned adjacent head end 36 and his or her feet will be positioned adjacent foot end 38.

Litter frame 28 provides a structure for supporting support deck 30, footboard 32, and side rails 34. Support deck 30 provides a support surface for a mattress (not shown in FIG. 1), such as, but not limited to, an air, fluid, or gel mattress. Alternatively, another type of soft cushion may be supported on support deck 30 so that a person may comfortably lie and/or sit thereon. The top surface of the mattress or other cushion forms a support surface for the occupant. Support deck 30 is made of a plurality of sections, some of which are pivotable about generally horizontal pivot axes. In the embodiment shown in FIG. 1, support deck 30 includes a head section 40, a seat section 42, a thigh section 44, and a foot section 46. Head section 40, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 44 and foot section 46 may also be pivotable about generally horizontal pivot axes.

Patient support apparatus 20 further includes a plurality of user interfaces 48 that enable a user of patient support apparatus 20, such as a patient and/or an associated caregiver, to control one or more aspects of patient support apparatus 20. In the embodiment shown in FIG. 1, patient support apparatus 20 includes a footboard user interface 48a, a pair of outer side rail user interfaces 48b (only one of which is visible), and a pair of inner side rail user interfaces 48c (only one of which is visible). Footboard user interface 48a and outer side rail user interfaces 48b are intended to be used by caregivers, or other authorized personnel, while inner side rail user interfaces 48c are intended to be used by the patient associated with patient support apparatus 20. Each of the user interfaces 48 includes a plurality of controls (not shown), although each user interface 48 does not necessarily include the same controls and/or functionality. In the illustrated embodiment, footboard user interface 48a includes a substantially complete set of controls for controlling patient support apparatus 20 while user interfaces 48b and 48c include a selected subset of those controls.

Among other functions, the controls of user interfaces 48 allow a user to control one or more of the following: change a height of support deck 30, raise or lower head section 40, activate and deactivate a brake for wheels 24, arm and disarm an exit detection system and, as will be explained in greater detail below, communicate with the particular IT infrastructure installed in the healthcare facility in which patient support apparatus 20 is positioned. One or both of the inner side rail user interfaces 48c also include at least one control that enables a patient to call a remotely located nurse (or other caregiver). In addition to the nurse call control, one or both of the inner side rail user interfaces 48c also include a speaker that enables the patient to hear the nurse's voice and a microphone that converts the patient's voice to audio signals that are transmitted to the nurse via a nurse call system.

Footboard user interface 48a is implemented in the embodiment shown in FIG. 1 as a control panel having a lid (flipped down in FIG. 1) underneath which is positioned a plurality of controls. As with all of the controls of the various user interfaces 48, the controls of user interface 48a may be implemented as buttons, dials, switches, or other devices. Any of user interfaces 48a-c may also include a display for displaying information regarding patient support apparatus 20. The display is a touchscreen in some embodiments.

Figure 2:
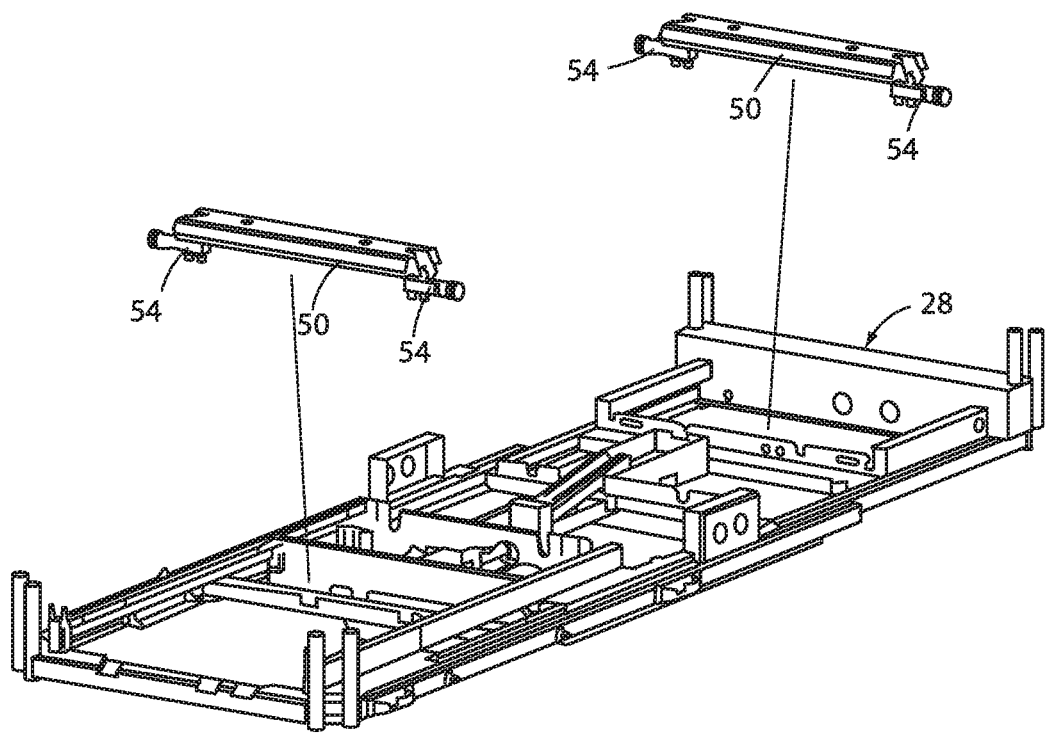
FIG. 2 is a perspective view of a litter frame and a pair of lift header assemblies of the patient support apparatus.

FIG. 2 illustrates in greater detail litter frame 28 separated from lifts 26 and base 22. Litter frame 28 is also shown in FIG. 2 with support deck 30 removed. Litter frame 28 is supported by two lift header assemblies 50. A first one of the lift header assemblies 50 is coupled to a top 52 (FIG. 3) of a first one of the lifts 26, and a second one of the lift header assemblies 50 is coupled to the top 52 of the second one of the lifts 26. Each lift header assembly 50 includes a pair of force sensors 54, which will be described herein as being load cells, but it will be understood that force sensors 54 may be other types of force sensors besides load cells. The illustrated embodiment of patient support apparatus 20 includes a total of four load cells 54, although it will be understood by those skilled in the art that different numbers of load cells may be used in accordance with the principles of the present disclosure. Load cells 54 are configured to support litter frame 28. More specifically, load cells 54 are configured such that they provide complete and exclusive mechanical support for litter frame 28 and all of the components that are supported on litter frame 28 (e.g. support deck 30, footboard 32, side rails 34, etc.). Because of this construction, load cells 54 are adapted to detect the weight of not only those components of patient support apparatus 20 that are supported by litter frame 28 (including litter frame 28 itself), but also any objects or persons who are wholly or partially being supported by support deck 30.

Figure 3:
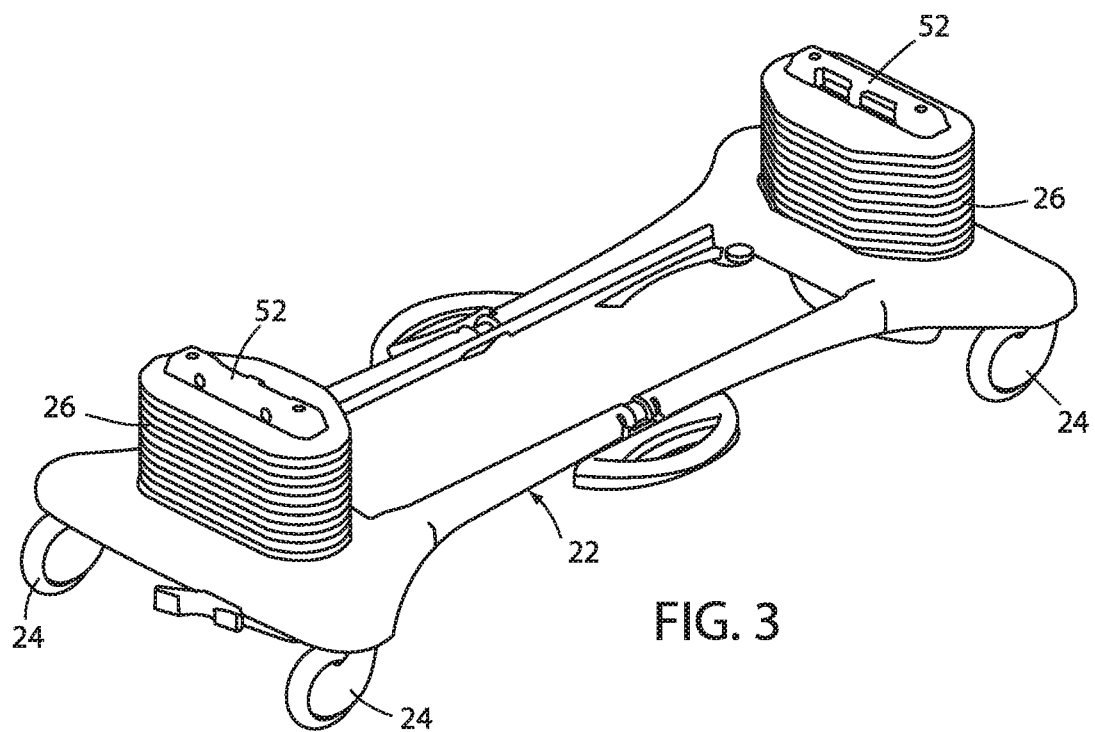
FIG. 3 is a perspective view of a base and a pair of lifts of the patient support apparatus.

The mechanical construction of patient support apparatus 20, as shown in FIGS. 1-3, is the same as, or nearly the same as, the mechanical construction of the Model 3002 S3 bed manufactured and sold by Stryker Corporation of Kalamazoo, Mich. This mechanical construction is described in greater detail in the Stryker Maintenance Manual for the MedSurg Bed, Model 3002 S3, published in 2010 by Stryker Corporation of Kalamazoo, Mich., the complete disclosure of which is incorporated herein by reference. It will be understood by those skilled in the art that patient support apparatus 20 can be designed with other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of patient support apparatus 20 may also take on forms different from what is disclosed in the aforementioned references.

Load cells 54 are part of an exit detection system 56 (FIG. 6) that, when armed, issues an alert when the patient exits from patient support apparatus 20. Exit detection system 56 is adapted to be armed via user interface 48. After being armed, exit detection system 56 determines when an occupant of patient support apparatus 20 has left, or is likely to leave, patient support apparatus 20, and issues an alert and/or notification to appropriate personnel so that proper steps can be taken in response to the occupant's departure (or imminent departure) in a timely fashion. In at least one embodiment, exit detection system 56 monitors the center of gravity of the patient using the system and method disclosed in commonly assigned U.S. Pat. No. 5,276,432 issued to Travis and entitled PATIENT EXIT DETECTION MECHANISM FOR HOSPITAL BED, the complete disclosure of which is incorporated herein by reference. In other embodiments, exit detection system 56 determines if the occupant is about to exit, or already has exited, from patient support apparatus 20 by determining a distribution of the weights detected by each load cell 54 and comparing the detected weight distribution to one or more thresholds. In such embodiments, the center of gravity may or may not be explicitly calculated.

Other manners for functioning as an exit detection system are also possible. These include, but are not limited to, any of the manners disclosed in the following commonly assigned patent applications: U.S. patent application Ser. No. 14/873,734 filed Oct. 2, 2015, by inventors Marko Kostic et al. and entitled PERSON SUPPORT APPARATUS WITH MOTION MONITORING; U.S. patent publication 2016/0022218 filed Mar. 13, 2014, by inventors Michael Hayes et al. and entitled PATIENT SUPPORT APPARATUS WITH PATIENT INFORMATION SENSORS; and U.S. patent application Ser. No. 15/266,575 filed Sep. 15, 2016, by inventors Anuj Sidhu et al. and entitled PERSON SUPPORT APPARATUSES WITH EXIT DETECTION SYSTEMS, the complete disclosures of all of which are incorporated herein by reference. Further, in some embodiments, load cells 54 may be part of both an exit detection system and a scale system that measures the weight of a patient supported on support deck 30. The outputs from the load cells 54 are processed, in some embodiments, in any of the manners disclosed in commonly assigned U.S. patent application Ser. No. 62/428,834 filed Dec. 1, 2016, by inventors Marko Kostic et al. and entitled PERSON SUPPORT APPARATUSES WITH LOAD CELLS, the complete disclosure of which is incorporated herein by reference.

Regardless of how implemented, patient support apparatus 20 is adapted to communicate an alert when the exit detection system is armed and detects that a patient is about to, or has, exited. The alert is communicated to a conventional nurse call system via a nurse call cable interface 58 or a nurse call wireless interface 60 onboard the bed (see FIG. 6). The alert may also be communicated elsewhere using other communication techniques (e.g. WiFi). The manner in which the alert is communicated to the nurse call system, as well as the manner in which the bed generally interacts with the existing IT infrastructure of a typical healthcare facility will now be described in more detail.

Figure 4:
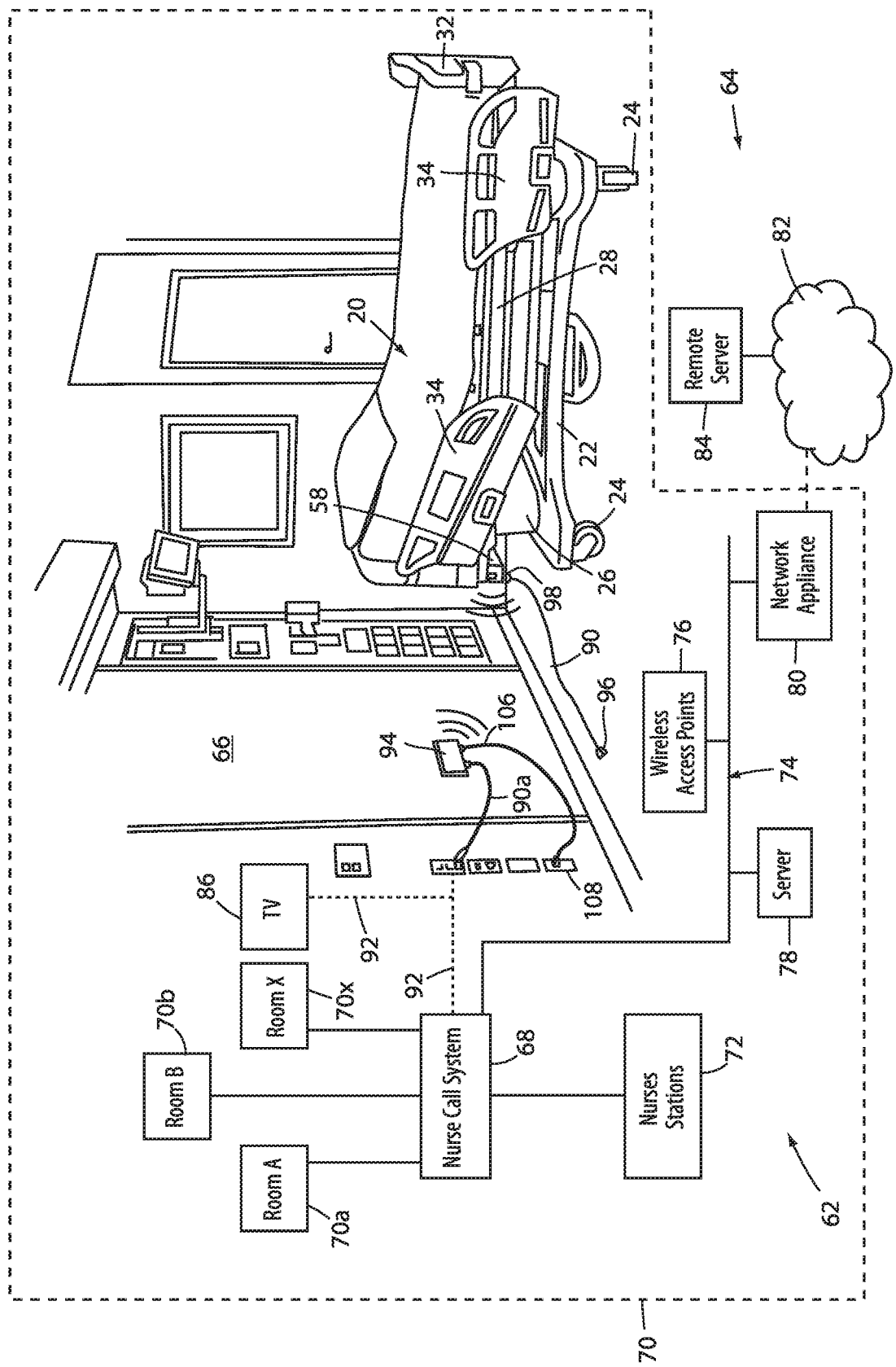
FIG. 4 is a diagram of the patient support apparatus shown communicatively coupled to a first embodiment of a wireless headwall module mounted in a room of a healthcare facility.

FIG. 4 illustrates patient support apparatus 20 coupled to the IT infrastructure 62 of a healthcare facility 64 according to one common configuration. As shown therein, healthcare facility 64 includes a headwall 66, a nurse call system 68, a plurality of rooms 70 (70a, 70b . . . 70x), one or more nurses' stations 72, a local area network 74, one or more wireless access points 76, a bed server 78, and one or more network appliances 80 that couple LAN 74 to the internet 82, thereby enabling servers and other applications on LAN 74 to communicate with computers outside of healthcare facility 64, such as, but not limited to, a geographically remote server 84. IT infrastructure 62 may be configured to interact with one or more room televisions 86. It will be understood by those skilled in the art that the particular components of the IT infrastructure 62 of healthcare facility 64 shown in FIG. 4 may vary widely. For example, patient support apparatus 20 may be used in healthcare facilities having no wireless access points 76, no connection to the internet 82 (e.g. no network appliances 80), and/or no bed server 78.

Still further, local area network 74 may include other and/or additional servers installed thereon, and nurse call system 68, in some healthcare facilities 64, may not be coupled to the local area network 74. Patient support apparatus 20 is capable of being installed in healthcare facilities 64 having still other variations of the IT infrastructure 62 illustrated in FIG. 4. It will therefore be understood that the particular IT infrastructure 62 shown in FIG. 4 is merely illustrative, and that patient support apparatus 20 is constructed to be communicatively coupled to IT infrastructures arranged differently from that of FIG. 4, some of which are discussed in greater detail below.

Patient support apparatus 20 is adapted to be communicatively coupled to a nurse call outlet 88 on headwall 66 by way of a cable 90 or wirelessly via a wireless headwall module 94. Wireless headwall module 94 communicates wirelessly with patient support apparatus 20 and, in the illustrated embodiment, includes a cable 90a that plugs into nurse call outlet 88. When patient support apparatus 20 is positioned in a room, such a room 70, and it is desired for patient support apparatus 20 to communicate with nurse call outlet 88 via a cable, cable 90a is unplugged from outlet 88 and replaced with cable 90. It will be understood that, in some rooms 70 and/or in some healthcare facilities, wireless headwall module 94 may not be present, and in such cases patient support apparatus 20 must communicate with nurse call outlet 88 via a cable 90. However, in those rooms 70 and/or healthcare facilities 64 in which one or more wireless headwall modules 94 are present, patient support apparatus 20 is configured with the option of utilizing either wired (e.g. cable 90) or wireless communication (via module 94) for its communications with nurse call outlet 88.

Nurse call outlet 88 is coupled to one or conductors 92 that electrically couple the nurse call outlet 88 to nurse call system 68 and to one or more other devices, such as television 86. Conductors 92 are typically located behind headwall 66 and not visible. In some healthcare facilities, conductors 92 may first couple to a room interface board that includes one or more electrical connections electrically coupling the room interface board to television 86 and/or nurse call system 68. Still other communicative arrangements for coupling nurse call outlet 88 to nurse call system 68 and television 86 are possible.

Cable 90 (FIG. 4) enables patient support apparatus 20 to communicate with nurse call system 68 and/or television 86. A patient supported on patient support apparatus 20 who activates a nurse call control on patient support apparatus 20 causes a signal to be conveyed via cable 90 to the nurse call system 68, which then sends a notification to one or more remotely located nurses (e.g. nurses at one of the nurses' stations 72). If the patient uses a TV control positioned on one of the user interfaces (e.g. user interface 48c) to change a channel or change the volume of television 86, the control conveys a signal along cable 90 to the nurse call outlet 88, and the signal is thereafter passed from outlet 88 to television 86. As will be discussed in greater detail below, cable 90 often includes a plurality of pins (e.g. 37 pins), and the audio signals that are passed between the patient when positioned on the patient support apparatus 20 and a remotely positioned nurse are transmitted over a separate set of pins than the control signals used to control television 86. Additional pins are used for communicating other information between patient support apparatus 20 and nurse call system 68 and/or other devices positioned within room 70 (e.g. television 86).

In order for patient support apparatus 20 to properly communicate with nurse call system 68, patient support apparatus 20 needs to be configured in a manner that physically matches the particular nurse call outlet 88 and that functionally matches how the nurse call system 68 utilizes the pins of nurse call outlet 88. In other words, different healthcare facilities 64 may utilize different brands and/or models of nurse call systems 68, and such different systems may utilize different types of nurse call outlets 88. One manner of ensuring patient support apparatus 20 is able to communicate with the particular nurse call system 68 within a given healthcare facility 64 is to utilize a customized cable 90 that correctly routes the pins of the cable 90 that are coupled to nurse call outlet 88 to the pins of cable 90 that are coupled to patient support apparatus 20. Other manners of ensuring the patient support apparatus 20 is properly configured to talk to nurse call system 68 via cable 90 are disclosed in commonly assigned U.S. patent application Ser. No. 15/945,437 filed Apr. 4, 2018, by inventors Krishna Bhimavarapu et al. and entitled PATIENT SUPPORT APPARATUSES WITH RECONFIGURABLE COMMUNICATION, the complete disclosure of which is incorporated herein by reference. Still other manners of configuring patient support apparatus 20 to match the existing nurse call system 68 may be utilized.

Figure 6:
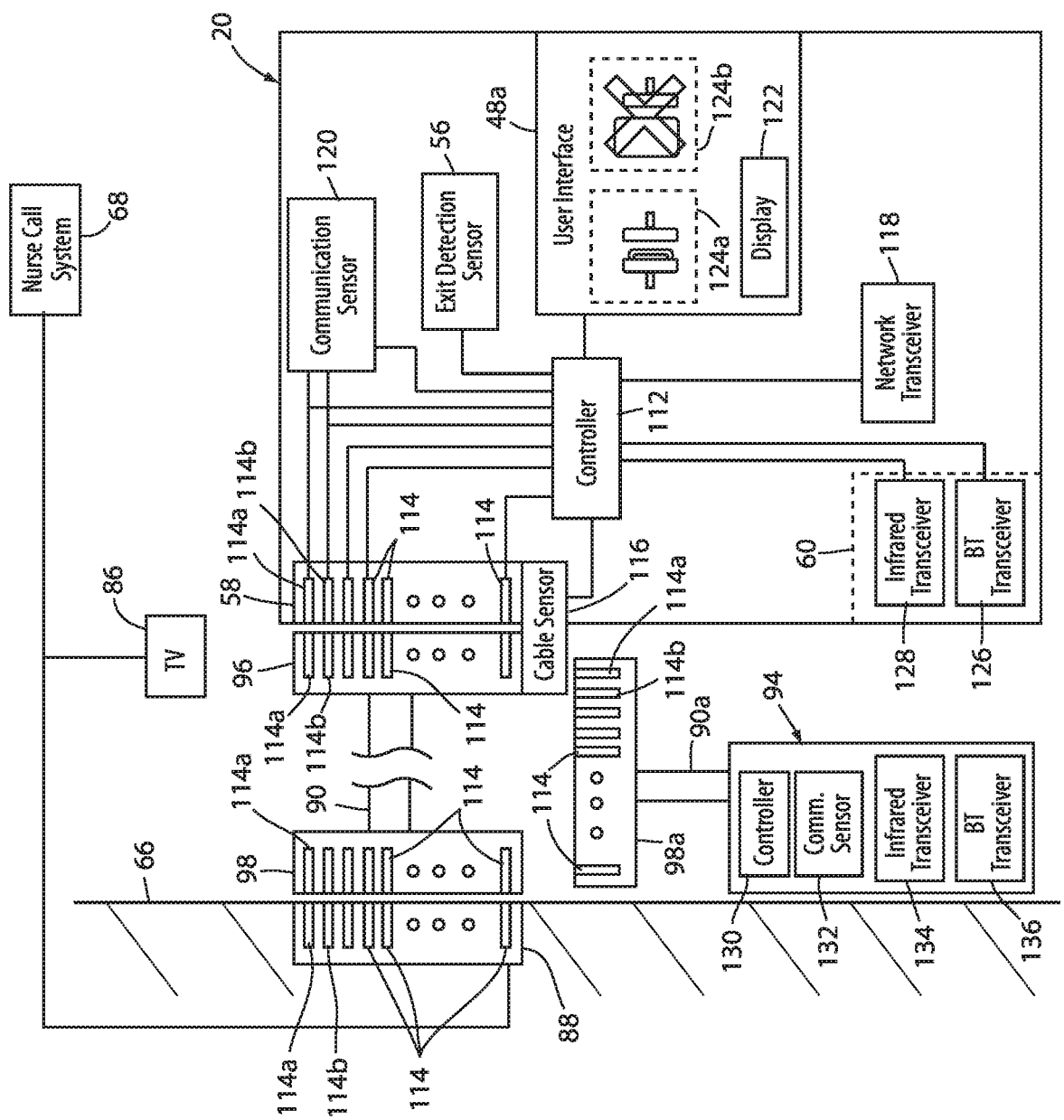
FIG. 6 is a block diagram of several of the structures of FIG. 4 showing some of the internal components of the wireless headwall module and the patient support apparatus.
Figure 15:
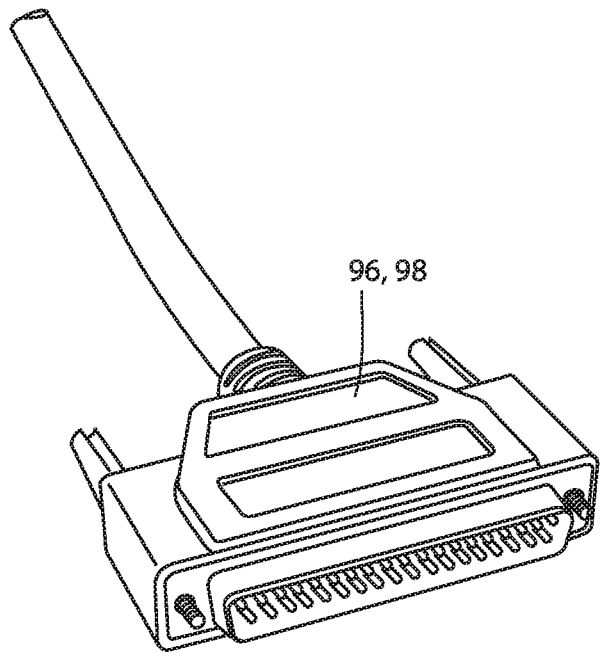
FIG. 15 is a perspective view of a prior art 37-pin male cable connector.
Figure 16:
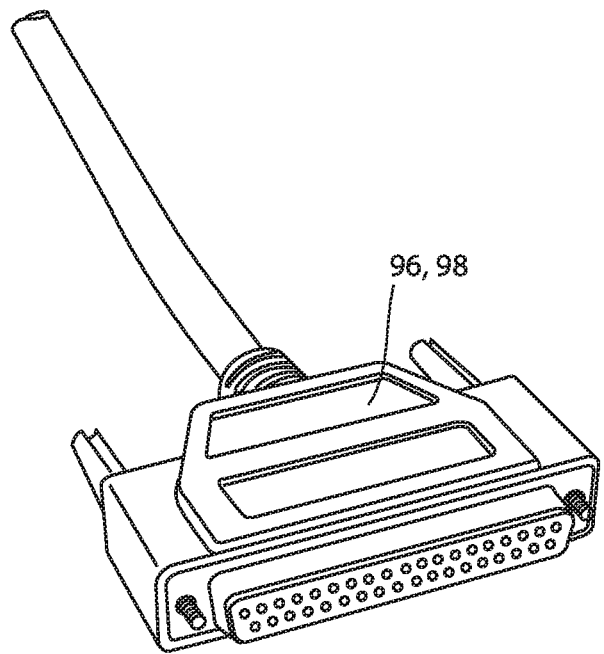
FIG. 16 is a perspective view of a prior art 37-pin female cable connector.

Cable 90 includes a first end having a first connector 96 and a second end having a second connector 98 (FIG. 4). First connector 96 is adapted to be plugged into a nurse call cable interface 58 positioned on patient support apparatus 20 (FIG. 6). Second connector 98 is adapted to be plugged into nurse call outlet 88. In many healthcare facilities 64, nurse call outlet 88 is configured as a 37-pin receptacle. In such facilities, cable 90 includes first and second connectors 96 and 98 having 37 pins (one of which may be a male connector and the other of which may be a female connector, although other combinations may be used). One example of a male 37-pin connector 96, 98 that may be used as first or second connector 96 or 98 is shown in FIG. 15. One example of a female 37-pin connector 96, 98 that may be used as first or second connector 96 or 98 is shown in FIG. 16. Other types of 37-pin connectors may also be used, depending upon the configuration of nurse call outlet 88. Still further, in some healthcare environments, nurse call outlet 88 includes fewer pins and/or has an arrangement of pins that is shaped to match a cable 90 having connectors different from what is shown in FIGS. 16 and 17. Patient support apparatus 20 is adapted to communicate with all of these different types of nurse call outlets 88 via an appropriately selected cable (e.g. one with the proper connectors 96, 98 on its ends).

Cable 90a, like cable 90, includes an end having a connector 96a that is adapted to couple to nurse call outlet 88. Connector 96a of cable 90a may be the same as connector 96 of cable 90. Connector 96a is therefore able to be plugged into outlet 88 instead of connector 96, and vice versa, depending upon whether patient support apparatus 20 is to communicate with nurse call system 68 via a wired connection or via a wireless connection.

Figure 5:
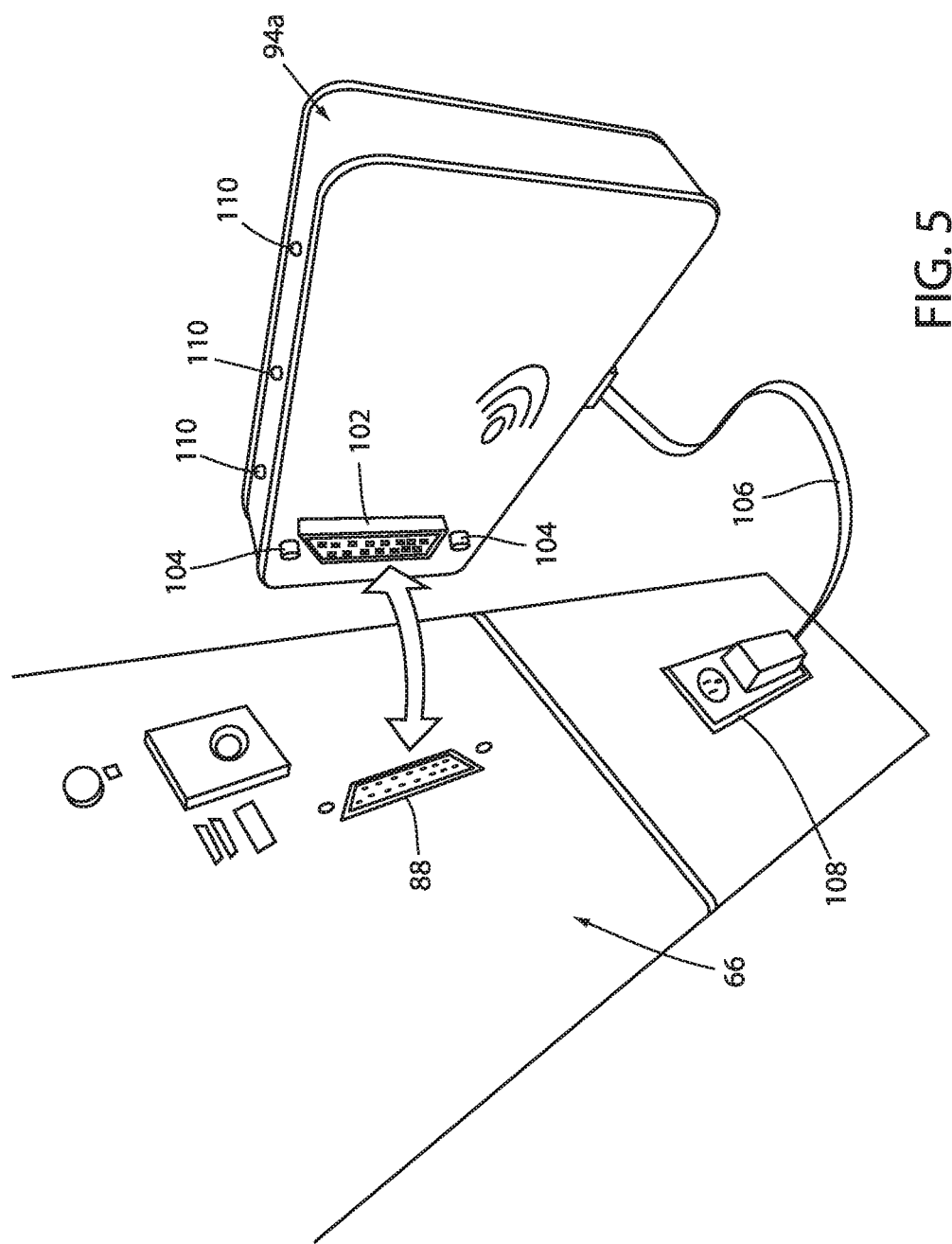
FIG. 5 is a perspective view of a second embodiment of a wireless headwall module that may be used to communicate with the patient support apparatus.

FIG. 5 illustrates a headwall module 94a according to another embodiment of the present disclosure. Headwall module 94a differs from headwall module 94 in that, rather than including a cable 90a, it is adapted to plug directly into nurse call outlet 88 via a connector 102. Connector 102 is thus shaped and dimensioned to be frictionally maintained in an electrically coupled state to outlet 88, and to support the entire headwall module 94a. One or more alignment posts 104 may be included with connector 102 in order to more securely retain headwall module 94a to nurse call outlet 88, if desired. Connector 102 may be the same as, or nearly the same as, 1ˢᵗ connector 96 of cable 90a, thereby allowing either headwall module 94 or headwall module 94a to be used for a given nurse call outlet 88.

In the embodiment shown in FIG. 5, connector 102 is a 37 pin connector that includes 37 pins adapted to be inserted into 37 mating sockets of nurse call outlet 88. As noted, such 37 pin connections are one of the most common types of connectors found on existing headwalls of medical facilities for making connections to the nurse call system 68. Such 37 pin connectors, however, are not the only type of connectors, and it will be understood that headwall module 94a can utilize different types of connectors 102 (whether integrated therein or attached to a cable) that are adapted to electrically couple to different types of nurse call outlets 88. One example of such an alternative nurse call outlet 88 and cable is disclosed in commonly assigned U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION, the complete disclosure of which is incorporated herein by reference. Still other types of nurse call outlets 88 and corresponding cable connectors 102 may be utilized.

Other than the absence of a cable 90a, headwall module 94a may be the same as headwall module 94, and the following description of headwall module 94 will apply equally to both headwall module 94 and headwall module 94a. Headwall module 94 of FIG. 4 (and headwall module 94a of FIG. 5) includes an electrical cable 106 having an end adapted to be inserted into a conventional electrical outlet 108. Electrical cable 106 enables headwall module 94 to receive power from the mains electrical supply via outlet 108. It will be appreciated that, in some embodiments, headwall module 94 is battery operated and cable 106 may be omitted. In still other embodiments, headwall module 94 may be both battery operated and include cable 106 so that in the event of a power failure, battery power supplies power to headwall module 94, and/or in the event of a battery failure, electrical power is received through outlet 108.

Headwall module 94 may also include a plurality of status lights 110, such as are shown in FIG. 5. Status lights 110 provide visual indications about one or more aspects of headwall module 94. For example, in some embodiments, the illumination of one of status lights 110 indicates that headwall module 94 is in successful communication with nurse call system 68 and/or patient support apparatus 20. The illumination of one or more additional status lights 110 may also or alternatively indicate that power is being supplied to headwall module 94 and/or the status of a battery included within headwall module 94. Still further, in some embodiments, one or more of status lights 110 may be illuminated depending upon whether a nurse is talking to the patient, or vice versa, via certain pins of module 94.

Headwall module 94 of FIG. 4 (and headwall module 94a of FIG. 5) is adapted to wirelessly receive signals from patient support apparatus 20 and deliver the signals to nurse call outlet 88 in a manner that matches the way the signals would otherwise be delivered to nurse call outlet 88 if a conventional nurse call cable (e.g. cable 90) were connected between patient support apparatus 20 and nurse call outlet 88. In other words, patient support apparatus 20 and headwall module 94 cooperate to provide signals to nurse call outlet 88 in a manner that is transparent to nurse call outlet 88 and nurse call system 68 such that these components cannot detect whether they are in communication with patient support apparatus 20 via wired or wireless communication. In this manner, a healthcare facility can utilize the wireless communication abilities of one or more patient support apparatuses 20 without having to make any changes to their existing nurse call outlet 88 or to their nurse call system 68.

In addition to sending signals received from patient support apparatus 20 to nurse call outlet 88, headwall module 94 is also adapted to forward signals received from nurse call outlet 88 to patient support apparatus 20. Headwall module 94 is therefore adapted to provide bidirectional communication between patient support apparatus 20 and nurse call outlet 88. Such bidirectional communication includes, but is not limited to, communicating audio signals between a person supported on patient support apparatus 20 and a nurse positioned remotely from patient support apparatus 20 (e.g. nurses' station 72). The audio signals received by headwall module 94 from patient support apparatus 20 are forwarded to nurse call outlet 88, and the audio signals received from nurse call outlet 88 are forwarded to one or more speakers onboard patient support apparatus 20.

Headwall module 94 also communicates the data and signals it receives from patient support apparatus 20 to the appropriate pins of nurse call outlet 88. Likewise, it communicates the data signals it receives and/or detects on the pins of nurse call outlet 88 to patient support apparatus 20 via wireless messages. The wireless messages include sufficient information for patient support apparatus 20 to discern what pins the messages originated from, or sufficient information for patient support apparatus 20 to decipher the information included in the message. In at least one embodiment, headwall module 94 includes any and/or all of the same functionality as, and/or components of, the headwall unit 76 disclosed in commonly assigned U.S. patent application Ser. No. 16/215,911 filed Dec. 11, 2018, by inventors Alexander Bodurka et al. and entitled HOSPITAL HEADWALL COMMUNICATION SYSTEM, the complete disclosure of which is incorporated herein by reference. Alternatively, or additionally, headwall module 94 may include any and/or all of the same functionality as, and/or components of, the headwall interface 38 disclosed in commonly assigned U.S. patent publication 2016/0038361 published Feb. 11, 2016, entitled PATIENT SUPPORT APPARATUSES WITH WIRELESS HEADWALL COMMUNICATION, and filed by inventors Krishna Bhimavarapu et al., the complete disclosure of which is also incorporated herein by reference. Still further, headwall module 94 and/or patient support apparatus 20 may include any of the functionality and/or components of the headwall modules 140, 140a and/or patient support apparatuses 20, 20a, and/or 20b disclosed in commonly assigned U.S. patent application Ser. No. 62/833,943 filed Apr. 15, 2019, by inventors Alexander Bodurka et al. and entitled PATIENT SUPPORT APPARATUSES WITH NURSE CALL AUDIO MANAGEMENT, the complete disclosure of which is incorporated herein by reference.

Further details regarding the manner in which patient support apparatus 20 communicates with nurse call outlet 88, and vice versa, as well as the structures involved with that communication, are provided below and illustrated in FIG. 6. As shown therein, patient support apparatus 20 includes nurse call cable interface 58, nurse call wireless interface 60, a controller 112, a cable sensor 116, a network transceiver 118, a communication sensor 120, exit detection system 56, and one or more user interfaces 48 (only user interface 48a is shown in FIG. 6, but it will be understood that the functions discussed below with respect to user interface 48a may be implemented on other ones of the user interfaces 48b and/or 48c).

Nurse call cable interface 58 is adapted to electrically couple to the plurality of pins 114 of cable connector 96. It will be understood that, although FIG. 6 shows each of connectors 96 and 98, as well as nurse call outlet 88 and nurse call cable interface 58, having a plurality of pins 114, one or more of these devices (cable 90, nurse call cable interface 58, and nurse call outlet 88) will include pin receptacles instead of pins. Such pin receptacles are adapted to receive and electrically couple to pins 114. Further, it will be understood that it does not matter which of these devices includes pins and which includes pin receptacles so long as each connection between the devices include a combination of pins and pin receptacles that allow communication between the mated devices. Consequently, the term "pins" as used herein will refer to pins and/or pin receptacles.

In some embodiments, controller 112 is implemented as, and/or includes, one or more conventional microcontrollers. In other embodiments, controller 112 may be modified to use a variety of other types of circuits—either alone or in combination with one or more microcontrollers—such as, but not limited to, any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by the microcontroller (if included) when carrying out the functions described herein, as well as the data necessary for carrying out these functions, are stored in a memory (not shown) that is accessible to controller 112.

It will be understood that nurse call outlet 88, cable 90, and nurse call cable interface 58 are all illustrated in FIG. 6 as having only six pins. This is done merely for purposes of compact illustration. All of these components typically include 37 pins, although there are other nurse call outlets having different pin numbers and the principles of the present disclosure can be applied in healthcare facilities having these types of nurse call systems as well. The pins that are not shown in FIG. 6 are used by other components of patient support apparatus 20 for other purposes. For example, one pin may be used to convey information to a nurse call system 68 and/or an intermediate structure along the path of conductor 92 (e.g. a room interface board) indicating whether the patient has pressed a control on patient support apparatus 20 to turn on or turn off a light in the particular room in which patient support apparatus 20 is located. Another pin may communicate that the status of a component onboard patient support apparatus 20, such as, but not limited to whether one or more side rails 34 are in a down position (or an up position); whether the position of any of the side rails 34 changes from an initial state; whether a brake on patient support apparatus 20 is set; whether the exit detection system is armed; whether support deck 30 is at its lowest height; whether head section 40 has pivoted to less than a threshold angle (e.g. 30 degrees); and whether patient support apparatus 20 has been set or not to monitor a particular set of conditions. These various items of data are detected by one or more corresponding sensors onboard patient support apparatus 20 that are in communication with nurse call cable interface 58. Still others of the additional pins may be used for still other purposes.

Although FIG. 6 illustrates a number of the pins 114 of nurse call cable interface 58 being fed directly to controller 112, it will be understood that this is done merely for purposes of illustrative convenience, and that one or more of these pins 114 may be fed to one or more intermediary structures before being fed to controller 112. Such intermediary structures may include, but are not limited to, one or more relays and/or switches whose states are controlled by controller 112. Additionally, some pins may not be coupled to controller 112, but may be routed to other structures within patient support apparatus 20.

Controller 112 communicates with cable sensor 116, communication sensor 120, exit detection system 56, user interface 48*a*, network transceiver 118, and nurse call wireless interface 60. Cable sensor 116 is adapted to detect when nurse call cable 90 is physically coupled to nurse call cable interface 58, as well as to detect when nurse call cable 90 is not physically coupled to nurse call cable interface 58. Cable sensor 116 reports the detection of the presence or absence of nurse call cable 90 being physically coupled to nurse call cable interface 58 to controller 112. Controller 112 uses this information for one or more purposes, including, but not limited to, notifying a user of patient support apparatus 20 via user interface 48*a*.

In some embodiments, user interface 48*a* includes a display 122 (FIG. 6) and a plurality of indicators 124*a*, 124*b*, etc. In some embodiments, the display 122 may take on the form and/or functionality of the display 64*a* disclosed in commonly assigned U.S. patent application Ser. No. 62/864,638 filed Jun. 21, 2019, by inventors Kurosh Nahavandi et al. and entitled PATIENT SUPPORT APPARATUS WITH CAREGIVER REMINDERS, the complete disclosure of which is incorporated herein by reference. Still other types of displays may also be used. User interface 48*a* may also include a dashboard of the type disclosed in the aforementioned patent application. Indicators 124*a* and/or 124*b* may be part of the dashboard. Still further, patient support apparatus 20 may be configured to issue any of the reminders in any of the manners disclosed in the aforementioned patent application. Other types of user interfaces 48*a*, however, may alternatively be used.

Each indicator 124*a* and 124*b* of user interface 48*a* is adapted to be illuminated by light of one or more colors. In some embodiments, indicators 124*a* and 124*b* are icons that are backlit by one or more lights, such as, but not limited to, light emitting diodes. Controller 112 is adapted to illuminate, in at least one embodiment, indicator 124*a* in a particular color (e.g. red or amber) when cable sensor 116 detects no nurse call cable 90 physically coupled to nurse call cable interface 58. In this embodiment, controller 112 may be configured to illuminate indicator 124*a* in a different color (e.g. green) when cable sensor 116 detects nurse call cable 90 is physically coupled to nurse call cable interface 58. Indicator 124*a* is therefore configured to provide a visual indication to the caregiver associated with patient support apparatus 20 in order to remind the caregiver to plug in a nurse call cable 90 to nurse call cable interface 58.

As an alternative to icons that are backlit, indicators 124*a* and/or 124*b* may be icons that are displayed on display 122 and whose color and/or other characteristics are changed based upon the state of cable sensor 116 (e.g. whether a cable 90 is detected or not). Still further, multiple icons 124*a* may be provided, one of which is illuminated when nurse call cable 90 is coupled to nurse call cable interface 58, and the other of which is illuminated when no nurse call cable 90 is coupled to nurse call cable interface 58. As yet another alternative, only a single indicator 124*a* may be included that is only illuminated when no cable 90 is detected, and which is unilluminated when cable 90 is detected (or, alternatively, vice versa). Still other manners of controlling one or more indicators 124a and/or 124b may be implemented by controller 112.

In addition to, or in lieu of, cable sensor 116, patient support apparatus 20 may include communication sensor 120. Communication sensor 120 is adapted to detect when patient support apparatus 20 is in communication with nurse call outlet 88. Communication sensor 120 therefore differs from cable sensor 116 in that it is able to detect communication with nurse call outlet 88 (and thus nurse call system 68), whereas cables sensor 116 only detects the physical present of cable 90. It is therefore possible that a cable 90 could be coupled to patient support apparatus 20 at one end but have its other end disconnected from nurse call outlet 88. In this particular situation, cable sensor 116 would detect cable 90 is coupled to patient support apparatus 20, but communication sensor 120 would detect that the cable 90 is not coupled to the nurse call outlet 88. Communication sensor 120 therefore detects when patient support apparatus 20 is in communication with nurse call outlet 88, while cable sensor 116 detects the physical presence of cable 90. In some embodiments, as will be discussed in more detail below, patient support apparatus 20 only includes a single one of these sensors (either cable sensor 116 or communication sensor 120), while in other embodiments (such as illustrated in FIG. 6), patient support apparatus 20 includes both sensors.

In one embodiment, communication sensor 120 detects communication between patient support apparatus 20 and nurse call outlet 88 by monitoring the voltage, if any, on at least two pins 114a and 114b of nurse call cable interface 58. In such embodiments, the two pins are what is commonly referred to as the Nurse Call Plus (+) pin and what is commonly referred to as the Priority Normally Open/Normally Closed (NO/NC) pin. FIG. 17 illustrates a typical arrangement and identification of the pins for a common 37-pin connector. As can be seen therein, pin twenty-five corresponds to the Nurse Call Plus (+) pin, and pin thirty corresponds to the Priority Normally Open/Normally Closed pin. Accordingly, when communication sensor 120 is coupled to a nurse call cable interface 58 having the pin arrangement shown in FIG. 17, communication sensor 120 detects the voltage, if any, on both pins twenty-five and thirty, which correspond to pins 114a and 114b of FIG. 6. If communication sensor 120 detects a voltage on one or both of these pins, it forwards a message to controller 112 indicating that a communication channel is currently established between patient support apparatus 20 and nurse call outlet 88. If no voltage is detected on either of these pins, communication sensor 120 forwards a message to controller 112 indicating that no communication channel has been established between patient support apparatus 20 and nurse call outlet 88.

Communication sensor 120 monitors the voltage on the two pins 114a and 114b because it has been found that most manufacturers of nurse call systems 68 will generate a voltage on either or both of these pins of their respective nurse call outlets 88. Such voltage typically, although not necessarily always, ranges from about five to twenty-seven volts. Communication sensor 120, in at least one embodiment, is constructed to detect any voltage that is greater than about 0.3 volts (positive or negative), although it will be understood that this threshold detection level may be changed. If a voltage of about 0.3 volts or greater is detected on either pin 114a or pin 114b, or on both of them, communication sensor 120 concludes that a communication channel currently exists between patient support apparatus 20 and nurse call outlet 88 (and thus nurse call system 68), and sends a message to controller 112 indicating the existence of this communication channel, as mentioned. If no voltage of about 0.3 volts or greater is detected on either of pins 114a or 114b, communication sensor 120 concludes that this communication is not present and forwards a message indicating such to controller 112.

In some embodiments, patient support apparatus 20 is configured to control the illumination of indicator 124a based solely upon the output of communication sensor 120. In these embodiments, if no voltage is detected on both pins 114a and 114b, controller 112 illuminates indicator 124a in a red or amber color, and if communication sensor 120 detects voltage on one or both of these pins 114a and/or 114b, controller 112 illuminates indicator 124a in a green color. Any of the alternative forms of illumination and/or variations of indicator 124 that were discussed above with respect to controller 112's interaction with cable sensor 116 may also or alternatively be implemented. In at least one of these embodiments, patient support apparatus 20 does not include a cable sensor 116.

In some other embodiments, patient support apparatus 20 is configured to control the illumination of indicator 124a based solely upon the output of cable sensor 116. In these embodiments, controller 112 controls the illumination of indicator 124a in any of the manners previously described based upon the output of cable sensor 116. In at least one of these embodiments, patient support apparatus 20 does not include a communication sensor 120.

In still another embodiment, controller 112 may be configured to control indicator 124a based upon outputs from both cable sensor 116 and communication sensor 120. In such embodiments, controller 112 may be configured to only indicate that a successful connection between the patient support apparatus 20 and nurse call outlet 88 has been established when both sensors 116 and 120 are in agreement as to the existence of this communication connection. That is, controller 112 may be configured to illuminate indicator 124a in a green color, for example, only when cable sensor 116 detects a cable 90 is present and communication sensor 120 detects a voltage on at least one of pins 114a and/or 114b. If either sensor 116 fails to detect a cable 90 or sensor 120 fails to detect a communication channel, then controller 112 controls the illumination of indicator 124a to indicate that no communication channel currently exists between patient support apparatus 20 and nurse call outlet 88 (e.g. indicator 124a is illuminated in a red color). Still other manners of controlling the illumination of indicator 124a may be utilized that are based on the outputs of both sensors 116 and 120.

In some embodiments, patient support apparatus 20 is also, or alternatively, configured to communicate with nurse call outlet 88 in a wireless manner (e.g. without cable 90). In such embodiments, patient support apparatus 20 includes nurse call wireless interface 60 adapted to communicate with the wireless headwall module 94. Nurse call wireless interface 60, in the example of FIG. 6, includes a Bluetooth transceiver 126 and an infrared transceiver 128. Wireless headwall module 94 includes a controller 130, a communication sensor 132, an infrared transceiver 134, and a Bluetooth transceiver 136. IR transceiver 134 of wireless headwall module 94 is adapted to communicate using infrared signals with IR transceiver 128 of patient support apparatus 20. Bluetooth transceiver 136 of wireless headwall module 94 is adapted to communicate using Bluetooth communications with Bluetooth transceiver 126 of patient support apparatus 20.

Controller 130 communicates with communication sensor 132, transceivers 134 and 136, as well as with additional electronics that are present on headwall module 94. The additional electronics may include any of the electronics disclosed in any of the following commonly assigned patent applications, and wireless headwall module 94 may be configured to perform any of the functions disclosed in the following commonly assigned patent applications: Ser. No. 16/215,911 filed Dec. 11, 2018, by inventors Alexander Bodurka et al. and entitled HOSPITAL HEADWALL COMMUNICATION SYSTEM; Ser. No. 16/217,203 filed Dec. 12, 2018, by inventor Alexander Bodurka, and entitled SMART HOSPITAL HEADWALL SYSTEM; and Ser. No. 16/193,150 filed Nov. 16, 2018, by inventors Alexander Bodurka et al. and entitled PATIENT SUPPORT APPARATUSES WITH LOCATION/MOVEMENT DETECTION, the complete disclosures of all of which are incorporated herein by reference.

Wireless headwall module 94 includes a cable 90*a* having a connector 98*a* that is adapted to be inserted into nurse call outlet 88. The additional electronics of wireless headwall module 94 may also include a nurse call cable interface that communicates with cable 90*a* and connector 98*a* in the same manners as nurse call cable interface 58 communicates with cable 90 and first connector 96. That is, the signals on the various pins of 114 of nurse call outlet 88 are communicated to controller 130 via cable 90*a* and controller 130 is adapted to forward those signals to nurse call wireless interface 60 of patient support apparatus 20 using transceivers 134 and/or 136. Likewise, wireless headwall module 94 is adapted to receive data from patient support apparatus 20 via one or both of transceivers 134 and/or 136 and to forward the received data, as appropriate, to corresponding pins 114 of connector 98*a* (which are then forwarded to nurse call outlet 88 when connector 98*a* is inserted therein).

Infrared transceiver 134 of headwall module 94 acts as a location transceiver. Infrared transceiver 134 is a short range transceiver that emits a short range signal containing an identifier that is unique to that particular wireless headwall module. Infrared transceiver 128 of patient support apparatus 20 is able to detect the short range signal from infrared transceiver 134 when the patient support apparatus 20 is positioned adjacent to headwall module 94 (e.g. within approximately a meter or two). Patient support apparatus 20 forwards this unique signal to an off board server, such as server 78 and/or remote server 84, which contains a table correlating the unique identifiers of each headwall module 94 to their location within the healthcare facility. Server 78 is therefore able to determine the location of each patient support apparatus 20 within the healthcare facility whenever the patient support apparatus 20 is positioned adjacent a headwall module 94. Further explanation of one manner in which transceivers 126, 128, 134, and 136 may operate are provided in the following commonly assigned U.S. patent applications: Ser. No. 16/215,911 filed Dec. 11, 2018, by inventors Alexander Bodurka et al. and entitled HOSPITAL HEADWALL COMMUNICATION SYSTEM; Ser. No. 16/217,203 filed Dec. 12, 2018, by inventor Alexander Bodurka, and entitled SMART HOSPITAL HEADWALL SYSTEM; and Ser. No. 16/193,150 filed Nov. 16, 2018, by inventors Alexander Bodurka et al. and entitled PATIENT SUPPORT APPARATUSES WITH LOCATION/MOVEMENT DETECTION, the complete disclosures of all of which are incorporated herein by reference.

Bluetooth transceivers 126 and 136 are used by controllers 112 and 130, respectively, to transmit audio signals between patient support apparatus 20 and wireless headwall module 94, such as, but not limited to, the audio signals used to convey the voice signals of the patient and the remotely positioned nurse. Such audio signals may also include the audio signals from television 86 and/or a radio or other entertainment device positioned in the room 70. Bluetooth transceivers 126 and 136 may also be used to transmit other data, such as, but not limited to, status data regarding the status of patient support apparatus 20, one or more messages indicating an exit detection alert has been issued, and/or other data. In some embodiments, wireless headwall module 94 and patient support apparatus 20 are configured to exchange audio signals therebetween in any of the manners disclosed in commonly assigned U.S. patent application Ser. No. 62/833,943 filed Apr. 15, 2019, by inventors Alexander Bodurka et al. and entitled PATIENT SUPPORT APPARATUSES WITH NURSE CALL AUDIO MANAGEMENT, the complete disclosure of which is incorporated herein by reference.

In many embodiments, infrared transceivers 128 and 134 are used to establish the Bluetooth communication link between patient support apparatus 20. In such embodiments, transceivers 128 and 134 may exchange a unique patient support apparatus ID and a unique wireless headwall module ID. These IDs are then used as addresses for the wireless communication between patient support apparatus 20 and wireless headwall module 94. Still other ways of communicating between patient support apparatus 20 and wireless headwall module 94 may be utilized.

Communication sensor 132 of wireless headwall module 94 operates in the same manner as communication sensor 120 of patient support apparatus 20. That is, communication sensor 132 is electrically coupled to pins 114*a* and 114*b* (corresponding to the Nurse Call Plus (+) and Priority Normally Open/Normally Closed (NO/NC) pins) and checks to see if a voltage is detected on either or both of these pins. If it detects a voltage on either or both of these pins, it concludes that connector 98*a* of cable 90*a* is coupled to nurse call outlet 88. If it does not detect a voltage on at least one of these pins, it concludes that connector 98*a* of cable 90*a* is not coupled to nurse call outlet 88. The coupling of connector 98*a* of cable 90*a* to nurse call outlet 88 replaces the coupling of connector 98 of cable 90 to nurse call outlet 88. In other words, nurse call outlet 88 is adapted to receive only a single cable, either cable 90 or cable 90*a*. Patient support apparatus 20 therefore communicates with nurse call outlet 88 either via cable 90 or wirelessly via wireless headwall module 94. When it communicates via cable 90, second connector 98 of cable 90 is inserted into nurse call outlet 88. When it communicates wirelessly via wireless headwall module 94, second connector 98*a* of cable 90*a* is inserted into nurse call outlet 88.

In at least one embodiment, controller 130 of wireless headwall module 94 is configured to report both of the outputs of communication sensor 132 (i.e. whether cable 90*a* is coupled or not coupled to nurse call outlet 88) to patient support apparatus 20. That is, controller 130 uses Bluetooth transceiver 136 (or IR transceiver 134, in some embodiments), to transmit a message to patient support apparatus 20 indicating whether connector 98*a* of cable 90*a* is connected to nurse call outlet 88 or not. In at least one embodiment, patient support apparatus 20 includes a separate indicator 124*b* that controller 112 controls in order to indicate to the user the status of wireless headwall module 94 vis-a-vis nurse call outlet 88. In such embodiments, controller 112 may be configured to illuminate indicator 124*b* in a first color (e.g. red or amber) if wireless headwall module 94 transmits a message to patient support apparatus 20 indicating that cable 90a is not coupled to nurse call outlet 88 (as detected by communication sensor 132), and to illuminate indicator 124b in a second color (e.g. green) if wireless headwall module 94 transmits a message to patient support apparatus 20 indicating that cable 90a is coupled to nurse call outlet 88 (as also detected by communication sensor 132). In this manner, patient support apparatus 20 provides an indication to the user thereon of the communication status of wireless headwall module 94.

In an alternative embodiment, controller 112 of patient support apparatus 20 is configured to utilize the same indicator 124a to indicate the status of both nurse call cable interface 58 and nurse call wireless interface 60. That is, when either communication sensor 120 detects a connection to nurse call outlet 88 or communication sensor 132 detects a connection to nurse call outlet 88 (and reports this to controller 112 via nurse call wireless interface 60), controller 112 illuminates indicator 124a in a first color (e.g. green). Further, when neither communication sensor 120 nor communication sensor 132 detects a respective connection to nurse call outlet 88, controller 112 illuminates indicator 124a in a second color (e.g. amber or red). A caregiver can therefore look at the user interface 48a and indicator 124a of patient support apparatus 20 to immediately determine if the patient support apparatus 20 is communicatively coupled to nurse call system 68 or not.

In at least one embodiment, patient support apparatus 20 is configured to automatically select a communication method (wired or wireless) based on the signals received from communication sensors 120 (and/or cable sensor 116) and 132. In such embodiments, if communication sensor 120 detects a voltage on pins 114a and/or 114b (and/or cable sensor 116 detects the presence of cable 90), controller 112 automatically communicates with nurse call outlet 88 using nurse call cable interface 58. On the other hand, if communication sensor 132 detects a voltage on pins 114a and/or 114b and controller 130 sends a message indicating this detection to patient support apparatus 20 (and to controller 112), controller 112 automatically communicates with nurse call outlet 88 by sending messages to headwall module 94 using nurse call wireless interface 60. The communication may include not only the audio signals from the remote nurse and/or patient positioned on patient support apparatus 20, but also status data regarding patient support apparatus 20, such as, but not limited to, an alert status of exit detection system 56, the status of side rails 34 (e.g. raised or lowered), the status of a brake, the height of litter frame 28, and/or other status data.

In at least one embodiment, controller 112 is configured, after automatically selecting a wired or wireless communication method (e.g. interface 58 or 60), to continue to use the automatically selected communication method until it either receives a signal from one of the communication sensors 120 or 132 (or cable sensor 116) indicating that the currently selected communication method is no longer viable (e.g. a voltage on pins 114a or 114b is no longer detected) or it is instructed by a caregiver to switch communication methods. Thus, for example, if a caregiver unplugs cable 90 from nurse call outlet 88 and inserts cables 90a therein, the former will be detected by communication sensor 120 (and possibly cable sensor 116), while the latter will be detected by communication sensor 132. Based on the signals received from these two sensors 120 and 132, controller 112 will automatically switch from wired communication via interface 58 to wireless communication via interface 60. Patient support apparatus 20 will therefore automatically select whichever communication method is available without requiring any manual instructions or manipulation of any controls on any of the user interfaces 48 by the caregiver.

Network transceiver 118 (FIG. 6) is a wireless transceiver adapted to communicate with one or more wireless access points 76 of the healthcare facility's local area network 74. In some embodiments, transceiver 118 may be a WiFi transceiver adapted to transmit and receive wireless electrical signals using any of the various WiFi protocols (IEEE 802.11b, 801.11g, 802.11n, 802.11ac . . . , etc.). In other embodiments, network transceiver 118 may be a transceiver adapted to communicate using any of the frequencies, protocols, and/or standards disclosed in commonly assigned U.S. patent application Ser. No. 62/430,500 filed Dec. 6, 2016, by inventor Michael Hayes and entitled NETWORK COMMUNICATION FOR PATIENT SUPPORT APPARATUSES, the complete disclosure of which is incorporated herein by reference. In still other embodiments, transceiver 118 may be a wired transceiver that communicates with network 74 over a wired network, such as an Ethernet cable or the like. Regardless of whether transceiver 118 is a wired or wireless transceiver, it enables controller 112 to communicate with one or more servers on the healthcare facility's network 72, such as, but not limited to, patient support apparatus server 78.

Controller 112 uses network transceiver 118 to send messages to server 78 (and/or server 84) indicating its communication status with nurse call system 68. The communication status refers to whether patient support apparatus 20 is communicating via cable interface 58, wireless interface 60, or not communicating at all. In some embodiments, server 78 and/or server 84 are configured to share this data with one or more other devices within the healthcare facility. For example, in at least one embodiment, server 78 and/or server 84 are configured to transmit the communication status of patient support apparatus 20 to one more electronic devices, such as the electronic devices 104a and/or 104b disclosed in commonly assigned U.S. patent application Ser. No. 62/868,947 filed Jun. 30, 2019, by inventors Thomas Durlach et al. and entitled CAREGIVER ASSISTANCE SYSTEM, the complete disclosure of which is incorporated herein by reference.

Figure 7:
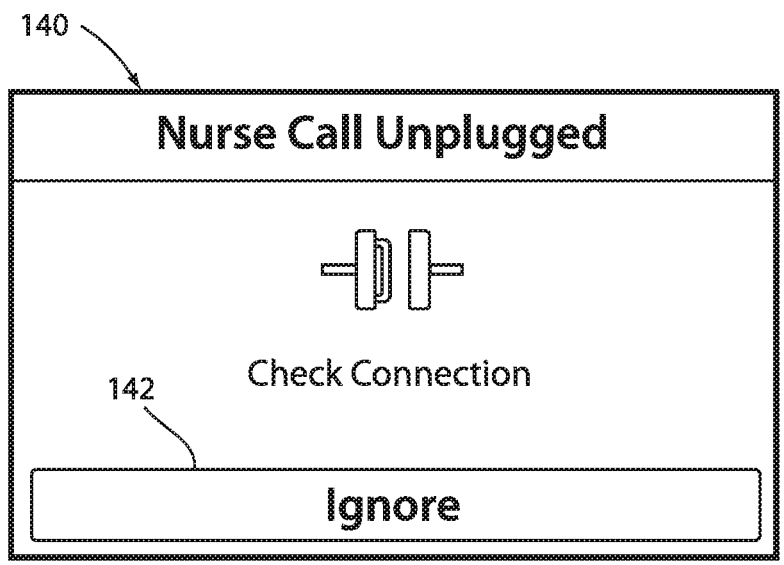
FIG. 7 is a popup window that may be displayed on a display of the patient support apparatus when cable communication between the patient support apparatus and the nurse call system is not operative.

FIG. 7 illustrates a popup window 140 that controller 112 is adapted to display on display 122 of user interface 48a when nurse call cable 90 is not coupled to patient support apparatus 20 and/or nurse call outlet 88. Thus, in those embodiments of patient support apparatus 20 having cable sensor 116 but not communication sensor 120, controller 112 is adapted to display window 140 when cable sensor 116 does not detect cable 90 coupled to nurse call cable interface 58. In those embodiments of patient support apparatus 20 having communication sensor 120 but not cable sensor 116, controller 112 is adapted to display window 140 when communication sensor 120 does not detect a voltage on either of pins 114a or 114b. In those embodiments of patient support apparatus 20 having both communication sensor 120 and cable sensor 116, controller 112 is adapted to display popup window 140 when either (or in some cases, both) sensors 116 and 120 fail to detect a connection to cable 90 or to nurse call outlet 88, respectively.

Popup window 140 is a dismissable popup. That is, window 140 includes an ignore control 142 that may be touched, or otherwise activated, by a user. When the ignore control 142 is activated, controller 112 ceases to display window 140 on display 122, and instead returns to displaying whatever content was previously displayed prior to displaying window 140. If the user does not touch the ignore control 142, controller 112 continues to display window 140 until the user corrects the communication connection between patient support apparatus 20 and nurse call system 68 (e.g. by plugging cable 90 into both nurse call outlet 88 and patient support apparatus 20). If the user touches the ignore control 142, controller 112 continues to illuminate indicator 124a in a manner that indicates that patient support apparatus 20 is not properly coupled to nurse call system 68 (and continues to do so until properly coupled thereto). In some embodiments, controller 112 is adapted to also cease displaying window 140 if nurse call wireless interface 60 establishes communication with wireless headwall module 94 and wireless headwall module 94 indicates that cable 90a is coupled to nurse call outlet 88.

Figure 8:
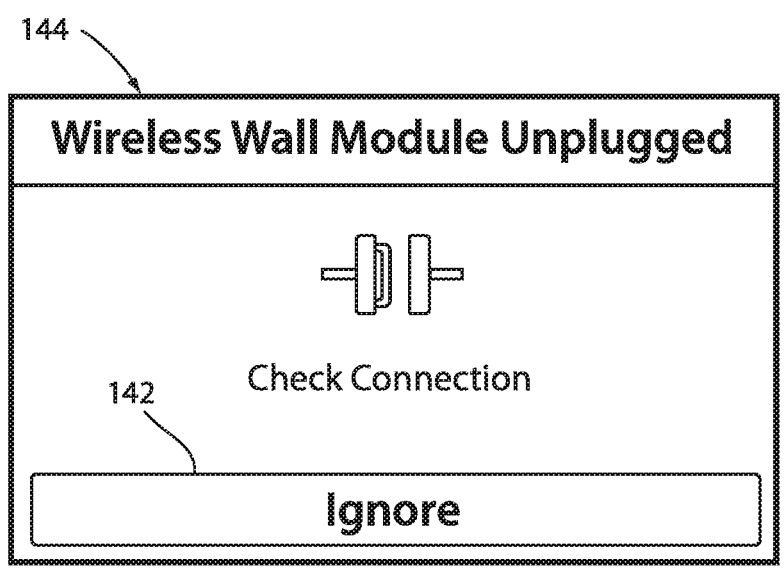
FIG. 8 is a popup window that may be displayed on a display of the patient support apparatus when cable communication between the wireless headwall module and the nurse call system is not operative.

FIG. 8 illustrates another popup window 144 that controller 112 is adapted to display on display 122 of user interface 48a when nurse call cable 90a of wireless headwall module 94 is not coupled to nurse call outlet 88. Thus, when controller 112 is in communication with wireless headwall module 94 and wireless headwall module 94 reports to controller 112 that its connector 98a is not coupled to nurse call outlet 88 (as detected by communication sensor 132), controller 112 is adapted to display popup window 144. As with popup window 140, window 144 is a dismissable popup window that includes an ignore control 142. Controller 112 continues to display window 144 until the user either activates ignore control 142 or cable 90a of wireless headwall module 94 is coupled to nurse call outlet 88. In some embodiments, controller 112 will also cease displaying window 144 if cable sensor 116 and/or communication sensor 120 detect a connection to cable 90 and/or to nurse call outlet 88, respectively.

Regardless of whether or not the user activates the ignore control 142 of window 144, controller 112 is configured to continue to illuminate indicator 124b in a manner that indicates that wireless headwall module 94 is not properly coupled to nurse call system 68 (and continues to do so until module 94 is properly coupled thereto, or patient support apparatus 20 is properly coupled thereto via nurse call wired interface 58).

Figure 9:
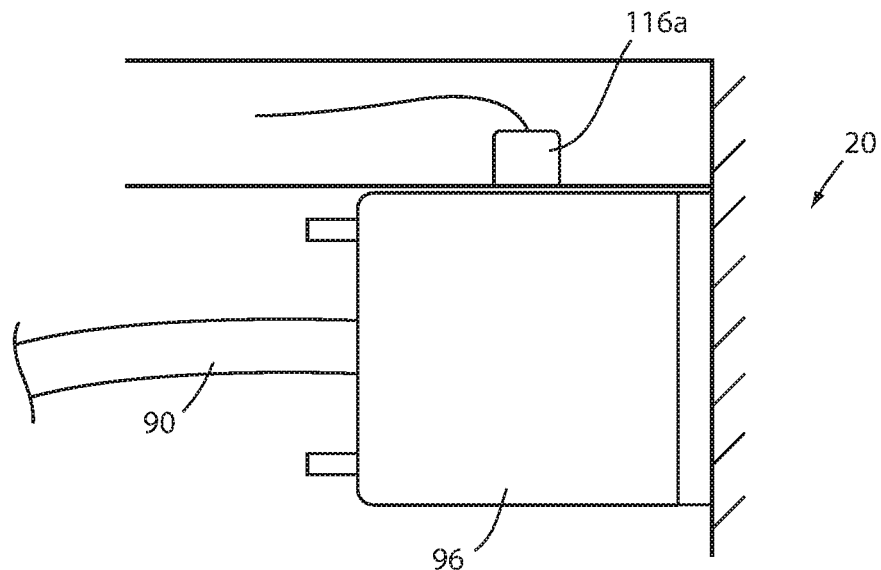
FIG. 9 is a plan view of a first embodiment of a cable sensor that may be used with the patient support apparatus to detect the presence/absence of a nurse call cable.

FIGS. 9-12 illustrate several different variations of cable sensor 116 that may be utilized with patient support apparatus 20. FIG. 9 illustrates a cable sensor 116a that is implemented as a Hall effect sensor. Cable sensor 116a is positioned on patient support apparatus 20 such that first connector 96 of cable 90 will be positioned adjacent to sensor 116a when connector 96 is coupled to nurse call wired interface 58 of patient support apparatus 20. When implemented in this manner, the Hall Effect sensor 116a may be a relatively high sensitivity sensor that detects changes in its voltage due to the presence or absence of the magnetic field generated by connector 96. Alternatively, a specialized connector 96 having a magnet integrated therein may be used, in which case Hall Effect sensor 116a may be a relatively low sensitivity sensor whose voltage varies in response to the adjacent presence of absence of connector 96. In either case, sensor 116a detects the presence or absence of connector 96 based upon the changes in its output voltage (due to the present or absent adjacent magnetic field of connector 96), and reports the absence or presence of connector 96 to controller 112.

Figure 10:
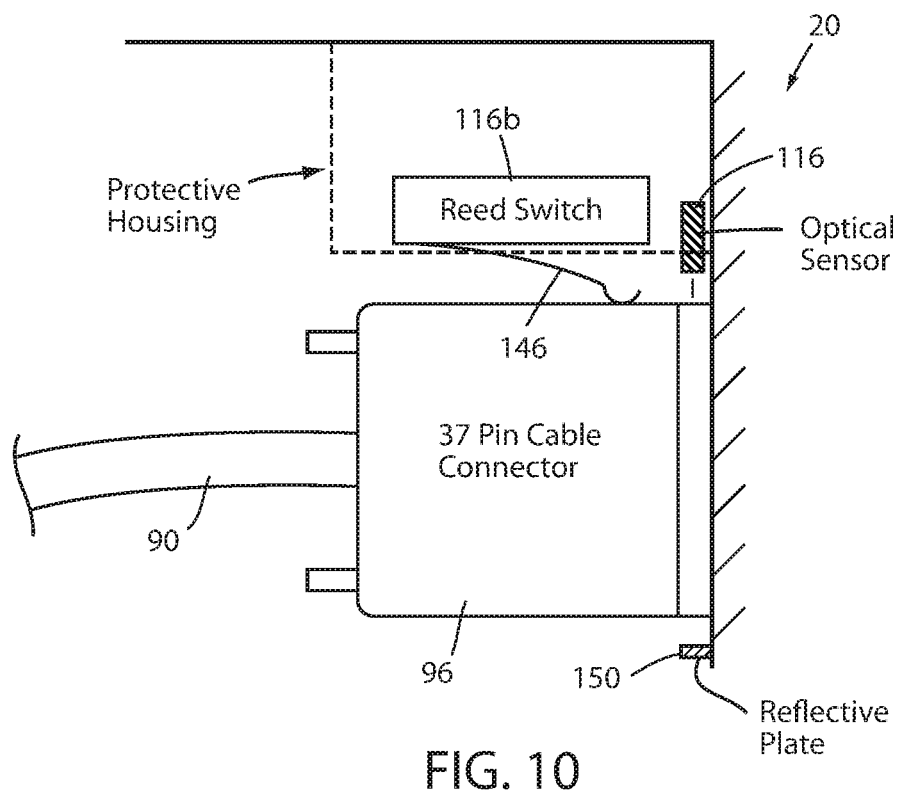
FIG. 10 is a plan view of second and third embodiments of a cable sensor that may be used with the patient support apparatus to detect the presence/absence of a nurse call cable.

FIG. 10 illustrates two cable sensors 116b and 116c. These two sensors 116b and 116c are illustrated as being combined onto a single patient support apparatus in FIG. 10, but this is merely done for purposes of drawing brevity. In an actual embodiment, patient support apparatus 20 will typically only include a single one of these sensors 116b or 116c (although, in some embodiments, multiple sensors 116 may be included).

Cable sensor 116b is a Reed switch having a flexible arm 146 that is pushed toward the body of the sensor 116b by connector 96 when connector 96 is coupled to patient support apparatus 20. Flexible arm 146 is biased outwardly from the body of sensor 116b such that when connector 96 is unplugged from patient support apparatus, flexible arm 146 flexes away from the body of sensor 116b to a greater extent than what is shown in FIG. 10. The position of flexible arm 146 is detected by Reed switch 116b and reported to controller 112.

Cable sensor 116c is an optical sensor that emits an optical beam across a portion of the port on patient support apparatus 20 into which cable connector 96 is to be inserted. When connector 96 is not coupled to patient support apparatus 20, the optical beam is emitted such that it impinges upon a reflective plate 150 that reflects the beam back toward optical sensor 116c. Optical sensor 116c includes a sensor that detects this reflected optical beam. Sensor 116c therefore detects the reflected beam when connector 96 is not coupled to patient support apparatus 20 and does not detect the reflected beam when connector 96 is coupled to patient support apparatus 20. Sensor 116c reports this absence or presence of cable connector 96 to controller 112.

Figure 11:
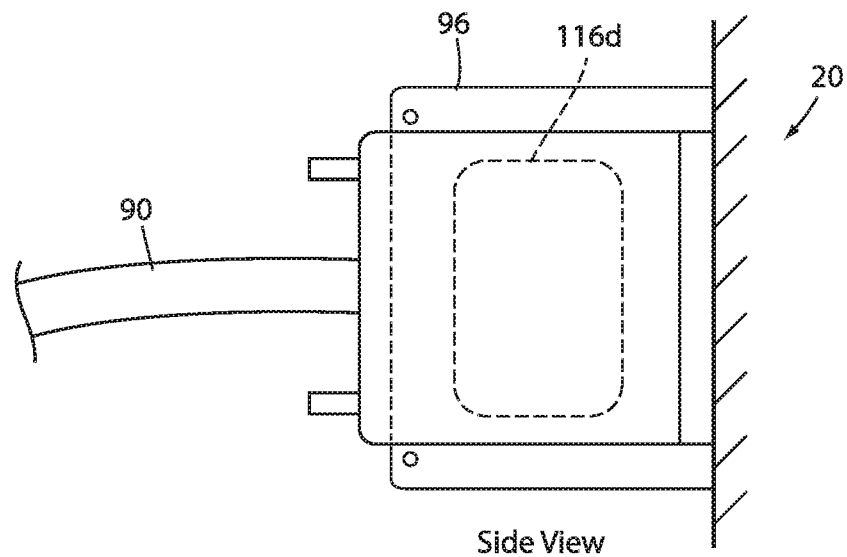
FIG. 11 is a side view of a fourth embodiment of a cable sensor that may be used with the patient support apparatus to detect the presence/absence of a nurse call cable.
Figure 12:
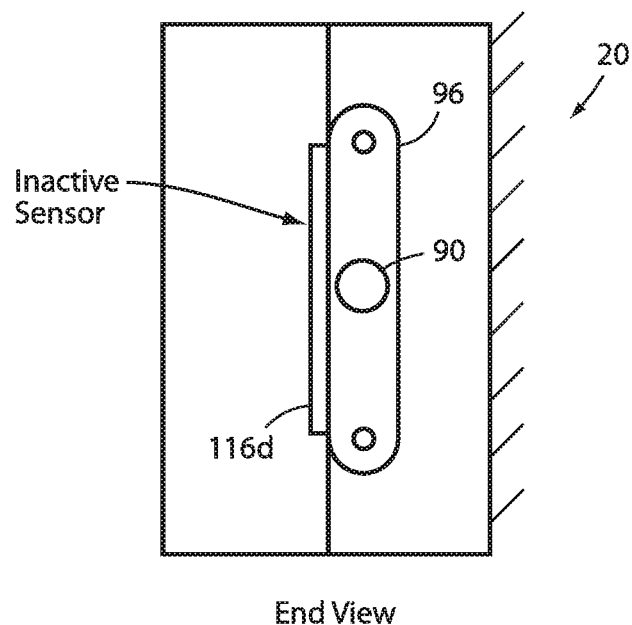
FIG. 12 is an end view of the fourth embodiment of a cable sensor that may be used with the patient support apparatus to detect the presence/absence of a nurse call cable.

FIG. 11 is a side view of another alternative cable sensor 116d that may be utilized with patient support apparatus 20. FIG. 12 illustrates cable sensor 116d from an end view. Cable sensor 116d is an inductive sensor that is adapted to detect changes in inductance due to the adjacent presence or absence of cable connector 96. In some embodiments, cable sensor 116 is shielded behind a plastic or non-ferrous material in order to shield itself from inductance changes due to sources other than the absence or presence of connector 96. Cable sensor 116d may utilize a resonant circuit whose resonance changes based on changes in inductance due to the absence or presence of connector 96, or cable sensor 116d may detect inductance changes in other manners. Cable sensor 116d reports the absence or presence of cable connector 96 to controller 112.

It will be understood that, although patient support apparatus 20 is shown in FIG. 6 as including both nurse call cable interface 58 and nurse call wireless interface 60, patient support apparatus 20 may be modified in some alternative embodiments to include only a single one of these interface 58, 60. When including only a single one of these interfaces, user interface 48a may further be modified to only include a single one of indicators 124a or 124b. Further, it will be understood that, although patient support apparatus 20 is shown in FIG. 6 as including both cable sensor 116 and communication sensor 120, patient support apparatus 20 may be modified in some alternative embodiments to include only a single one of these sensors 116, 120.

It will also be understood that still other modifications may be made to patient support apparatus 20 and/or wireless headwall module 94. For example, in any of the embodiments described herein, cable sensor 116 may be repositioned, or duplicated, at the opposite end of cable 90 (i.e. the end that couples to nurse call outlet 88) such that the coupling of cable 90 to nurse call outlet 88 is also, or alternatively, detected. Still further, for wireless headwall module 94a, which does not include a cable 90a, communication sensor 132 may be replaced by, or supplemented with, a sensor similar to cable sensor 116 that detects when connector 102 is coupled to nurse call outlet 88 by detecting the physical proximity of connector 102 to outlet 88, or vice versa.

In some alternative embodiments, communication sensors 120 and/or 132 are modified to monitor the voltage on more than the two pins mentioned above (i.e. the Nurse Call Plus (+) pin and the Priority Normally Open/Normally Closed (NO/NC) pin). For example, in at least one such modified embodiment, communication sensor 120 and/or 132 is modified to monitor the voltage on four pins: the Nurse Call Plus (+) pin, the Priority Normally Open/Normally Closed (NO/NC) pin, the Nurse Call Normally Open/Normally Closed (NO/NC) pin (pin 26 in FIG. 17), and the Priority Common pin (pin 31 in FIG. 17). In these modified embodiments, if voltage is detected on any of these four pins, controller 112 concludes that a successful connection has been established with the nurse call system. The addition of pins 26 and 31 (from FIG. 17) to the list of pins monitored by communication sensors 120 and/or 132 is included because it has been found that, in some nurse call systems, the polarity of pair of pins 25 and 26 (from FIG. 17) is reversed and/or the polarity of pins 30 and 31 (from FIG. 17) is reversed. By monitoring the voltage on all four of these pins, if any one of them have a non-zero voltage, controller 112 interprets this as due to a successful connection with the nurse call system.

Still further, in another alternative embodiment, communication sensors 120 and/or 132 may be modified to monitor the voltage on the Nurse Call Light+pin (pin 19 in FIG. 17) and the Nurse Call Light−pin (pin 28 in FIG. 17). These pins may be monitored in addition to, or in lieu of, any of the previously mentioned pins. It has been found that many nurse call systems will generate a relatively low voltage (e.g. about two volts) on at least one of these pins, even when no nurse call is taking place (the voltage increases when a nurse call takes place and the nurse call light is illuminated). Communication sensors 120 and/or 132 can therefore monitor the voltage on these pins to determine if a connection has been successfully established with the nurse call system.

In some embodiments, controller 112 concludes that a successful connection to the nurse call system has taken place only if multiple pins are detected with a non-zero voltage, and/or only if cable sensor 116 detects a cable. In other embodiments, controller 112 concludes that a successful connection to the nurse call system has taken place if any of one or more of the pins has a non-zero voltage, regardless of the other pin(s) and regardless of the output of cable sensor 116 (if included). Still other variations are possible.

Figure 13:
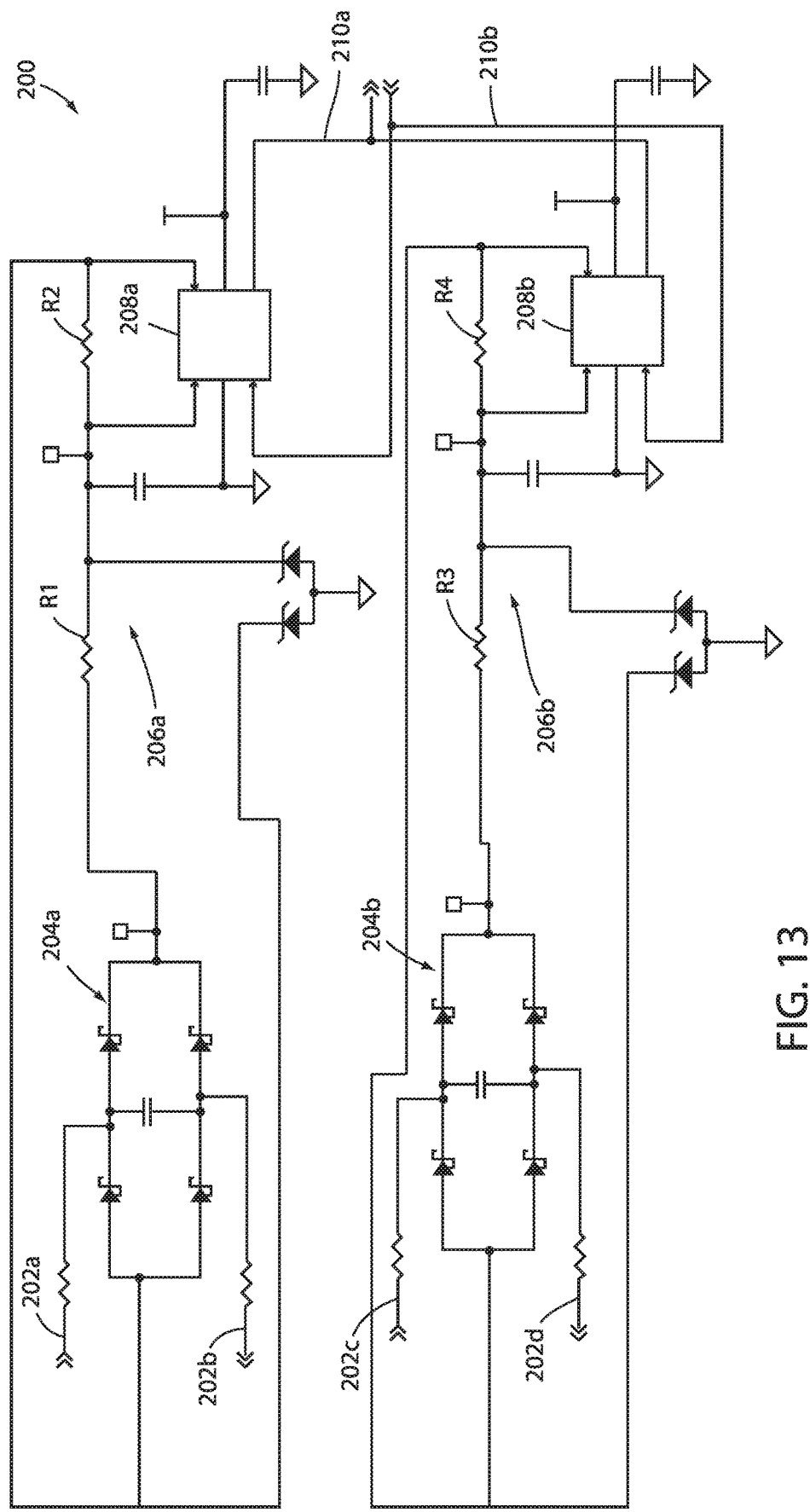
FIG. 13 is an electrical schematic of a first monitoring circuit that may be integrated into the patient support apparatus and/or the wireless headwall module for detecting a connection to the nurse call system.
Figure 14:
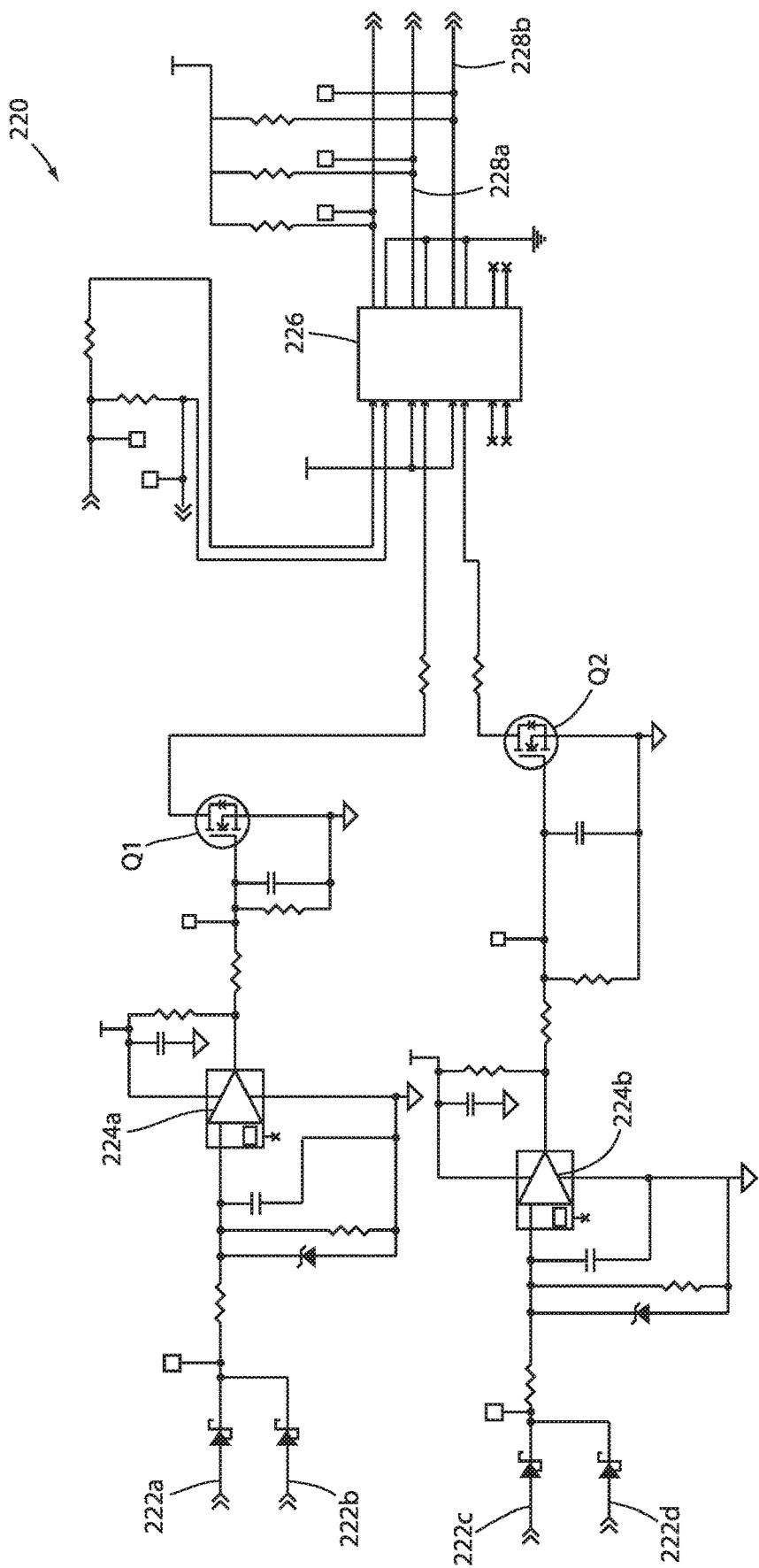
FIG. 14 is an electrical schematic of a second monitoring circuit that may be integrated into the patient support apparatus and/or the wireless headwall module for detecting a connection to the nurse call system, either in lieu of or in addition to, the first monitoring circuit.

In at least one embodiment, patient support apparatus 20 and/or wireless headwall module 94 includes both first monitoring circuit 200 and second monitoring circuit 220 (FIGS. 13 and 14, respectively). First monitoring circuit 200 includes four inputs 202a-d. Input 202a is electrically coupled to the positive nurse call answer light pin 114 of nurse call outlet 88 (pin 16 of FIG. 17). Input 202b is electrically coupled to the negative nurse call answer light pin 114 of nurse call outlet 88 (pin 29 of FIG. 17). Input 202c is electrically coupled to the positive nurse call light pin 114 of nurse call outlet 88 (pin 19 of FIG. 17), and input 202d is electrically coupled to the negative nurse call light pin 114 of nurse call outlet 88 (pin 28 of FIG. 17). First monitoring circuit is configured to detect any voltage between inputs 202a-b, as well as any voltage between inputs 202c-d. The first set of inputs 202a-b are fed to a first diode bridge 204a and the second set of inputs 202c-d are fed to a second diode bridge 204b. Diode bridges 204a-b act to allow the polarity of each of their respective inputs 202 to be reversed without affecting the detection of the voltage between these two pairs of inputs.

The output from first diode bridge 204a is fed to a first voltage divider 206a comprised of resistors R1 and R2. The output from second diode bridge 204b is fed to a second voltage divider 206b comprised of resistors R3 and R4. The voltage across resistor R2 is coupled to a first A/D converter 208a, and the voltage across the resistor R4 is coupled to a second A/D converter 208b. The outputs 210a,b of both first A/D converter 208a and second A/D converter 208b are fed to a microcontroller that is part of controller 112 (when first monitoring circuit 200 is included one patient support apparatus 20) or that is part of controller 130 (when first monitoring circuit 200 is included as part of wireless headwall module 94).

It can therefore be seen from FIG. 13 that if a positive voltage is present between inputs 202a and 202b, the digital value of this positive voltage will be fed to controller 112 or 130 on first output 210a. Similarly, if a positive voltage is present between inputs 202c and 202d, the digital value of this positive voltage will be fed to controller 112 or 130 on second output 210b. Controller 112 or 130 concludes that it is electrically coupled to nurse call outlet 88 if either output 210a or 210b has a non-zero voltage (or, in some embodiments, a non-zero voltage with an absolute value above a minimal threshold (e.g. 0.1 to 0.5 volts).

Turning to second monitoring circuit 220 (FIG. 14), it includes four inputs 222a-d. Input 222a is electrically coupled to the positive nurse call pin 114 of nurse call outlet 88 (pin 25 of FIG. 17). Input 222b is electrically coupled to the nurse call Normally Open/Normally Closed (NO/NC) pin 114 of nurse call outlet 88 (pin 26 of FIG. 17). Input 222c is electrically coupled to the Priority NO/NC pin 114 of nurse call outlet 88 (pin 30 of FIG. 17), and input 222d is electrically coupled to the Priority Common pin 114 of nurse call outlet 88 (pin 31 of FIG. 17). Second monitoring circuit 220 is configured to detect any voltage between inputs 222a-b, as well as any voltage between inputs 222c-d. The first set of inputs 222a-b are fed to a first low voltage comparator 224a and the second set of inputs 222c-d are fed to a second low voltage comparator 224b.

The output from first low voltage comparator 224a is fed to a first transistor Q1 and the output from the second low voltage comparator 224b is fed to a second transistor Q2. Depending on the voltages fed to transistors Q1 and Q2, the drains of each of the respective transistors are either switched to a low voltage state or a high voltage state. These respective states are coupled to a first side of an optical isolator 226. Optical isolator 226 has a second side coupled to first line 228a and second line 228b. Each line 228a and 228b is electrically coupled to the same microcontroller (part of controller 112 or 130) that outputs 210a and 210b of first circuit 200 are coupled to. Line 228a will therefore indicate to the microcontroller when a voltage is detected between inputs 222a and 222b. Similarly, lines 228b will indicate to the microcontroller when a voltage is detected between inputs 222c and 222d. Controller 112 or 130 concludes that it is electrically coupled to nurse call outlet 88 if either line 228a or 228b indicates a non-zero voltage (or, in some embodiments, a non-zero voltage with an absolute value above a minimal threshold (e.g. 0.1 to 0.5 volts).

In combination, controller 112 or 130 uses first and second monitoring circuits 200 and 220, in at least one embodiment, to detect if the patient support apparatus 20 or wireless headwall unit 94 is electrically coupled to nurse call outlet 88 by looking for voltages between any of the four following pairs of inputs: (1) inputs 202a and 202b; (2) inputs 202c and 202d; (3) inputs 222a and 222b; and (4) inputs 222c and 222d. If controller 112 or 130 detects a voltage on any one of these four pairs, it concludes that it is electrically coupled to the nurse call outlet 88. If it does not, it concludes there is no such connection and, in at least some embodiments, issues an alert.

In any of the embodiments discussed herein, patient support apparatus 20 and/or headwall unit 94 may be user-configurable with respect to notifications regarding a lack of connection with nurse call outlet 88. That is, in some embodiments, patient support apparatus 20 includes a screen, switch, or other control that enables a user to choose between first and second states for the detection of the connection to the nurse call outlet 88. In the first state, if the controller 112 or 130 does not detect a connection to the nurse call outlet 88, it issues an alert to the user (locally at headwall unit 94 and/or patient support apparatus 20; remotely at a nurses' station and/or a mobile electronic device in communication with patient support apparatus 20; or a combination of both). In the second state, if the controller 112 or 130 does not detect a connection to the nurse call outlet 88, it does not issue an alert. Alternatively, in the second state, the controller 112 and/or 130 may be configured to not even process the inputs indicative of whether or not it is connected to nurse call outlet 88.

By having two different states, a user can determine if he or she wants to receive alerts when either patient support apparatus 20 or wireless headwall module 94 is disconnected from the nurse call outlet 88. This can be useful if the user wishes to avoid nuisance alerts in situations where such a disconnection may be deliberate, common, and/or otherwise known to the user. In such situations, the user can select the second state (no alerts). Alternatively, if there are situations where the user wishes such alerts to be issued, he or she can select the first state.

In some embodiments, the selection between the first and second states is made by accessing user interface 48a onboard patient support apparatus 20. Alternatively, or additionally, the selection between the first and second states may be made by the user by accessing a switch, control, or other structure that is directly attached to headwall unit 94. Still further, user interface 48a may be configured to allow a user to select and the first or second state and then communicate that information to wireless headwall 94 via controller 112 and one or both of transceivers 126 and/or 128.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus comprising:
a litter frame;
a support deck supported by the litter frame, the support deck adapted to support a patient thereon;
a nurse call cable interface adapted to receive a first end of a nurse call cable, the nurse call cable including a second end adapted to couple to an outlet of a nurse call system, the outlet mounted to a headwall of a healthcare facility;
a communication sensor adapted to detect when a communication channel is successfully established between the nurse call cable interface and the nurse call system, and to detect when the communication channel is not successfully established between the nurse call cable interface and the nurse call system;
a display;
an indicator; and
a controller in communication with the communication sensor, the display, and the indicator, the controller adapted to activate the indicator when the communication sensor detects that the communication channel is not successfully established between the nurse call cable interface and the nurse call system, the controller further adapted to display a dismissible popup window on the display when the communication sensor detects that the communication channel is not successfully established between the nurse call cable interface and the nurse call system, and, in response to a user dismissing the popup window, to stop displaying the dismissible popup window but to continue to activate the indicator until the communication sensor detects the communication channel is successfully established between the nurse call cable interface and the nurse call system.

2. The patient support apparatus of claim 1 wherein the first end of the nurse call cable includes a 37-pin connector, the nurse call cable interface includes a complementary 37-pin connector, the communication sensor is a voltage sensor adapted to detect voltage on two of the pins, and the controller is adapted to conclude that the communication channel is successfully established when voltage is detected on either or both of the two pins.

3. The patient support apparatus of claim 2 wherein a first one of the two pins is a Nurse Call Plus pin and a second one of the two pins is a Priority Normally Open/Normally Closed (NO/NC) pin.

4. The patient support apparatus of claim 1 wherein the indicator comprises a light adapted to illuminate a nurse call connection icon and wherein the controller is adapted to activate the light with a green color when the communication sensor detects that the communication channel is successfully established between the nurse call cable interface and the nurse call system, and the controller is adapted to activate the light in a different color when the communication sensor detects that the communication channel is not successfully established between the nurse call cable interface and the nurse call system.

5. The patient support apparatus of claim 1 further comprising a wireless network transceiver adapted to communicate with a server on a local area network via a wireless access point of the local area network, wherein the controller is further adapted to send a message to the server when the communication sensor detects that the communication channel is not successfully established between the nurse call cable interface and the nurse call system.

6. The patient support apparatus of claim 1 further comprising a wireless transceiver adapted to wirelessly communicate with a headwall module mounted to the headwall of the healthcare facility.

7. The patient support apparatus of claim 6 wherein the controller is adapted to automatically send data to the nurse call system via the wireless transceiver when the communication sensor detects that the communication channel is not successfully established between the nurse call cable interface and the nurse call system, and to automatically send data to the nurse call system via the nurse call cable interface when the communication sensor detects that the communication channel is successfully established between the nurse call cable interface and the nurse call system.

8. The patient support apparatus of claim 1 further comprising a cable sensor adapted to detect when the nurse call cable is physically coupled to the nurse call cable interface and when the nurse call cable is not physically coupled to the nurse call cable interface, wherein the cable sensor comprises at least one of the following: (a) a Hall effect sensor adapted to detect a presence of the first end of the nurse call cable when the first end of the nurse call cable is plugged into the nurse call cable interface; (b) an inductive sensor adapted to detect a presence of the first end of the nurse call cable when the first end of the nurse call cable is plugged into the nurse call cable interface; (c) a Reed switch sensor adapted to detect a presence of the first end of the nurse call cable when the first end of the nurse call cable is plugged into the nurse call cable interface; or (d) an optical sensor adapted to detect a presence of the first end of the nurse call cable when the first end of the nurse call cable is plugged into the nurse call cable interface.

9. A patient support apparatus comprising:
a litter frame;
a support deck supported by the litter frame, the support deck adapted to support a patient thereon;
an exit detection system adapted to issue an alert when the exit detection system is armed and the patient exits the patient support apparatus;
a nurse call cable interface adapted to receive a first end of a nurse call cable, the nurse call cable including a second end adapted to couple to an outlet of a nurse call system, the outlet mounted to a headwall of a healthcare facility;
an indicator;
a wireless transceiver adapted to wirelessly communicate with a headwall module mounted to the headwall of the healthcare facility, the headwall module adapted to be physically coupled to the outlet, the wireless transceiver adapted to receive a message from the headwall module indicating that the headwall module is not communicatively coupled to the outlet of the nurse call system; and
a controller adapted to communicate the alert to the nurse call system when the exit detection system detects the patient has exited the patient support apparatus, the controller adapted to automatically select whether to communicate the alert to the nurse call system via the wireless transceiver or via the nurse call cable interface, the controller further adapted to activate the indicator when the wireless transceiver receives the message indicating that the headwall module is not communicatively coupled to the nurse call system.

10. The patient support apparatus of claim 9 further comprising a cable sensor adapted to detect when the nurse call cable is physically coupled to the nurse call cable interface and when the nurse call cable is not physically coupled to the nurse call cable interface, and wherein the controller is adapted to automatically select to communicate the alert to the nurse call system via the nurse call cable interface when the cable sensor detects that the nurse call cable is physically coupled to the nurse call cable interface, and to automatically select to communicate the alert to the nurse call system via the wireless transceiver when the cable sensor detects that the nurse call cable is not physically coupled to the nurse call cable interface.

11. The patient support apparatus of claim 9 further comprising a communication sensor adapted to detect when a communication channel is successfully established between the nurse call cable interface and the nurse call system, and to detect when the communication channel is not successfully established between the nurse call cable interface and the nurse call system; and wherein the controller is adapted to automatically select to communicate the alert via the wireless transceiver when the communication sensor detects that the communication channel is not successfully established between the nurse call cable interface and the nurse call system, and to automatically select to communicate the alert via the nurse call cable interface when the communication sensor detects that the communication channel is successfully established between the nurse call cable interface and the nurse call system.

12. The patient support apparatus of claim 11 wherein the first end of the nurse call cable includes a 37-pin connector, the nurse call cable interface includes a complementary 37-pin connector, the communication sensor is a voltage sensor adapted to detect voltage on two of the pins, the controller is adapted to conclude that the communication channel is successfully established when voltage is detected on either or both of the two pins, and a first one of the two pins is a Nurse Call Plus pin and a second one of the two pins is a Priority Normally Open/Normally Closed (NO/NC) pin.

13. The patient support apparatus of claim 11 further comprising a wireless network transceiver adapted to communicate with a server on a local area network via a wireless access point of the local area network, wherein the controller is further adapted to send a message to the server when the communication sensor detects that the communication channel is not successfully established between the nurse call cable interface and the nurse call system.

14. The patient support apparatus of claim 9 wherein the wireless transceiver is a Bluetooth transceiver, wherein the patient support apparatus further comprises an infrared transceiver adapted to communicate with the headwall module, and wherein the controller automatically pairs the patient support apparatus with the headwall module using information received from the headwall module via the infrared transceiver.

15. The patient support apparatus of claim 9 wherein the wireless transceiver is adapted to receive a message from the headwall module, the message indicating at least one of the following: (a) the headwall module is not physically coupled to the outlet of the nurse call system, or (b) the headwall module is physically coupled to the outlet of the nurse call system; and wherein the controller is adapted to use the message when selecting whether to communicate the alert to the nurse call system via the wireless transceiver or via the nurse call cable interface.

16. A patient support apparatus comprising:
a litter frame;
a support deck supported by the litter frame, the support deck adapted to support a patient thereon;
a nurse call cable interface adapted to receive a first end of a nurse call cable, the nurse call cable including a second end adapted to couple to an outlet of a nurse call system, the outlet mounted to a headwall of a healthcare facility;

a sensor adapted to detect if the nurse call cable interface is communicatively coupled to the outlet;

a wireless transceiver adapted to wirelessly communicate with a headwall module mounted to the headwall of the healthcare facility, the headwall module adapted to be physically coupled to the outlet, the wireless transceiver adapted to receive a message from the headwall module indicating that the headwall module is not communicatively coupled to the outlet of the nurse call system;

a first indicator;

a second indicator;

a user interface; and a controller in communication with the wireless transceiver, the sensor, and the user interface, the controller adapted to control the user interface to inform a caregiver when the sensor detects that the nurse call cable interface is not communicatively coupled to the outlet and to inform the caregiver when the wireless transceiver receives the message indicating that the headwall module is not communicatively coupled to the outlet of the nurse call system, the controller further adapted to activate the first indicator when the sensor detects that the nurse call cable interface is not communicatively coupled to the outlet and to activate the second indicator when the wireless transceiver receives the message indicating that the headwall module is not communicatively coupled to the nurse call system.

17. The patient support apparatus of claim 16 wherein the user interface includes a display and the controller is adapted to display a first message on the display when the sensor detects that the nurse call cable interface is not communicatively coupled to the outlet and to display a second message on the display when the wireless transceiver receives the message indicating that the headwall module is not communicatively coupled to the nurse call system.

18. The patient support apparatus of claim 16 wherein the sensor is a cable sensor adapted to detect when the nurse call cable is physically coupled to the nurse call cable interface and when the nurse call cable is not physically coupled to the nurse call cable interface, and wherein the cable sensor comprises at least one of the following: (a) a Hall effect sensor adapted to detect a presence of the first end of the nurse call cable when the first end of the nurse call cable is plugged into the nurse call cable interface; (b) an inductive sensor adapted to detect a presence of the first end of the nurse call cable when the first end of the nurse call cable is plugged into the nurse call cable interface; (c) a Reed switch sensor adapted to detect a presence of the first end of the nurse call cable when the first end of the nurse call cable is plugged into the nurse call cable interface; or (d) an optical sensor adapted to detect a presence of the first end of the nurse call cable when the first end of the nurse call cable is plugged into the nurse call cable interface.

* * * * *